US011389653B2

(12) United States Patent
Annetta et al.

(10) Patent No.: US 11,389,653 B2
(45) Date of Patent: Jul. 19, 2022

(54) ELECTRICAL STIMULATION DEVICES AND SYSTEMS FOR SAFELY OPERATING SUCH DEVICES

(71) Applicant: Battelle Memorial Institute, Columbus, OH (US)

(72) Inventors: Nicholas Annetta, Columbus, OH (US); Jeffrey Weisgarber, Jewett, OH (US); Noah Lemire, Columbus, OH (US); Matthew Edward Mowrer, Saint Clairsville, OH (US); Albert E. Weller, III, Columbus, OH (US); Alexander Campean, Stronsgville, OH (US); Matthew Staub, Columbus, OH (US); Andrew M. Schimmoeller, Plain City, OH (US); Jeffrey A. Friend, Grove City, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 47 days.

(21) Appl. No.: 16/708,918

(22) Filed: Dec. 10, 2019

(65) Prior Publication Data
US 2020/0188665 A1    Jun. 18, 2020

Related U.S. Application Data

(60) Provisional application No. 62/778,660, filed on Dec. 12, 2018.

(51) Int. Cl.
*A61N 1/36*    (2006.01)
*H03K 3/01*    (2006.01)
(Continued)

(52) U.S. Cl.
CPC ....... *A61N 1/36034* (2017.08); *A61N 1/0456* (2013.01); *A61N 1/16* (2013.01); *G05F 3/26* (2013.01); *H03K 3/01* (2013.01)

(58) Field of Classification Search
CPC ........ A61N 1/025; A61N 1/0456; A61N 1/16; A61N 1/3603; A61N 1/36034;
(Continued)

(56) References Cited

U.S. PATENT DOCUMENTS

| 4,273,132 A | 6/1981 | Hartlaub et al. |
| 7,463,931 B2 | 12/2008 | Foster et al. |

(Continued)

FOREIGN PATENT DOCUMENTS

WO    WO 2018/013884 A1    1/2018

OTHER PUBLICATIONS

International Search Report for PCT Application No. PCT/US2019/065388 dated Mar. 26, 2020.

*Primary Examiner* — Carl H Layno
*Assistant Examiner* — Jane C Kalinock
(74) *Attorney, Agent, or Firm* — Fay Sharpe LLP

(57) ABSTRACT

Portable high-voltage electrical stimulation devices and systems are disclosed that are scalable to utilize a minimal number of output channels to a large number of output channels. The devices and systems include a high-voltage power supply and output pulse circuitry comprising a plurality of output channel circuits. The electrical stimulation devices and systems disclosed herein also provide improved safety features, including an optional safety monitor.

20 Claims, 15 Drawing Sheets

(51) Int. Cl.
*G05F 3/26* (2006.01)
*A61N 1/04* (2006.01)
*A61N 1/16* (2006.01)

(58) Field of Classification Search
CPC .. A61N 1/36125; A61N 1/36142; G05F 3/26; H03K 3/01; H03K 3/26
USPC .......................................................... 607/59
See application file for complete search history.

(56) References Cited

U.S. PATENT DOCUMENTS

| | | |
|---|---|---|
| 8,515,545 B2 | 8/2013 | Trier |
| 8,615,306 B2 | 12/2013 | Griffith |
| 8,874,219 B2 | 10/2014 | Trier et al. |
| 8,923,962 B2 | 12/2014 | Libbus et al. |
| 9,717,904 B2 | 8/2017 | Simon et al. |
| 9,764,145 B2 | 9/2017 | Callas et al. |
| 2005/0245993 A1 | 11/2005 | Varrichio et al. |
| 2010/0069997 A1 | 3/2010 | Dupeyron |
| 2010/0106219 A1 | 4/2010 | Torgerson et al. |
| 2013/0090712 A1* | 4/2013 | Popovic ............. A61N 1/36167 607/148 |
| 2014/0277268 A1* | 9/2014 | Lee .................... A61N 1/36146 607/66 |
| 2015/0066108 A1* | 3/2015 | Shi ..................... A61N 1/36139 607/59 |
| 2017/0368329 A1* | 12/2017 | Tyler ................... A61M 21/00 |
| 2018/0071515 A1* | 3/2018 | Weiss ...................... A61N 1/36 |

* cited by examiner

ELECTRICAL STIMULATION DEVICES AND SYSTEMS FOR SAFELY OPERATING SUCH DEVICES

CROSS-REFERENCE TO RELATED APPLICATIONS

This application claims priority to U.S. Provisional Patent Application Ser. No. 62/778,660, filed Dec. 12, 2018, titled ELECTRICAL STIMULATION DEVICES AND SYSTEMS FOR SAFELY OPERATING SUCH DEVICES, the disclosure of which is herein incorporated by reference in its entirety.

BACKGROUND

The following relates generally to the neurostimulation arts, the neuromuscular electrical stimulation arts, the electrical muscle stimulation arts, the transcutaneous electrical neuromuscular stimulation arts, the functional electrical stimulation (FES) arts, and the electronic circuit topology arts related thereto. It finds particular application in association with high-voltage, portable, and scalable electrical stimulation arts.

The use of electrical stimulation for the treatment of medical conditions is well known, and the delivery of electrical current to a patient's muscles and/or nerves has a wide variety of therapeutic applications. Various invasive and non-invasive techniques and medical devices are currently available. However, each indication (i.e. medical condition or symptom to be treated) requires specifically calibrated electrical stimulation (e.g. pulse rate, voltage, current amplitude, pulse width, polarity, waveform, etc.) to achieve beneficial therapeutic results. Many of these techniques and devices carry the risk of limited beneficial results, and if not properly designed and implemented, carry the risk of significantly damaging the patients' tissues and/or worsening their condition. Moreover, some electrical stimulation applications involve the surgical implantation of electrodes within a patient, which further increases the risk to the patient's overall health.

In contrast, other applications of electrical stimulation, such as those discussed herein, are non-invasive, and do not require a break in the skin (or other surface of the body) or contact with an internal body cavity beyond a body orifice. These applications have the potential to reduce the damage to a patient's biological tissues and be suitable for use by the patient or family members in out-patient settings (e.g. at home, at work, etc.). In such applications, electrodes are applied non-invasively to the surface of a patient's body, and an electrical current is applied in specific patterns to the patient's muscles and/or nerves through the patient's skin.

However, such applications also have several drawbacks. Typical previous approaches require many components, and thus are either limited in size or application. In other words, a device with many electrical stimulation channels may require many electrical components, and therefore become bulky and not user-friendly. Alternatively, less complex devices with fewer channels are more portable, but are more limited in the range and nature of the stimulation they can provide, thus limiting their overall therapeutic efficacy. Additionally, even though such techniques and devices are non-invasive, they still carry the risk of damaging a patient's tissues (e.g. via over-stimulation) and/or not providing a beneficial therapeutic effect. Previous attempts at addressing these inherent risks have included, for example, using a low-voltage power supply, using multiple timing sources, and including additional level-shifting and/or logic circuitry in a high-voltage domain. Thus, these approaches also result in a similar tradeoff between size and complexity, portability and functionality.

Thus, it would be desirable to provide new systems, devices, and methods for electrical stimulation that is highly portable, scalable (i.e. incorporating a wide range of channels and/or electrodes), and user-friendly. Further, it would be desirable to provide such systems, devices, and methods that can safely operate at high voltages, without increasing the complexity of the system, while still delivering therapeutic electrical stimulation to the patient.

BRIEF DESCRIPTION

In accordance with one embodiment of the present disclosure, there is provided a multi-channel neurostimulation system comprising a high-voltage power supply, an output pulse circuitry operatively connected to the high-voltage power supply, a plurality of electrodes operatively connected to the output pulse circuitry, and a controller operatively connected to the output pulse circuitry. The controller is configured to instruct the output pulse circuitry to deliver an electrical output pulse via one or more of the plurality of electrodes. The output pulse circuitry comprises a plurality of output channel circuits, and each output channel circuit can include a high-voltage domain and a low-voltage domain. In particular, the high-voltage domain comprises a current source, a current mirror, and a channel output. Further, the low-voltage domain comprises a reference current generator, a source-side amplitude control, a current sink, and a sink-side amplitude control. In exemplary embodiments, the output current (i.e., stimulation current) can be limited by the minimum current set between channel pairs.

In particular embodiments, one or more of the components in the high-voltage domain of each output channel circuit has a voltage rating of at least about 20 V, or from about 20 V to about 1000 V, and the one or more of the components in the low-voltage domain of each output channel circuit has a voltage rating of at most 50 V, or from about 1.8 V to about 50 V. In further embodiments, the high-voltage power supply provides a voltage of from about 20 V to about 1000 V.

In some embodiments, the multi-channel neurostimulation system can include a safety monitor operatively connected to the controller and the output pulse circuitry. The safety monitor may be configured to receive one or more input signals from the controller (e.g. signals associated with an output pulse that is to be generated and delivered by the output pulse circuitry), and to output a stimulation disable signal to the output pulse circuitry. The stimulation disable signal can, for example, prevent the output pulse circuitry from generating and/or delivering a planned output pulse if a fault condition has been detected.

In accordance with another embodiment of the present disclosure, there is provided a portable multi-channel neurostimulation device comprising a high-voltage power supply, a plurality of electrodes, an output pulse circuitry operatively connected to the high-voltage power supply and the plurality of electrodes, and a controller operatively connected to the output pulse circuitry. The controller can be configured to instruct the output pulse circuitry to deliver an electrical output pulse via one or more of the plurality of electrodes. In particular, the output pulse circuitry comprises a plurality of output channel circuits, and each output channel circuit can include at least: a current source; a current mirror; a first resistor; a second resistor; a reference current generator; a source-side amplitude control; a current sink; a sink-side amplitude control; a source-side cascode element; a sink-side cascode element; a DC blocking capacitor; a discharge switch; and a channel output.

In particular embodiments, for each output channel circuit, the current source is operatively connected to the high-voltage power supply, the current mirror is operatively connected to the high-voltage power supply and the current source, the first resistor is operatively disposed between the high-voltage power supply and the current source, the second resistor is operatively disposed between the high-voltage power supply and the current mirror, the reference current generator is operatively connected to the current mirror, the source-side amplitude control is operatively connected to the reference current generator, the current sink is operatively connected to the current source, the source-side cascode element is operatively disposed between the current mirror and the reference current generator, the source-side enable is operatively connected to the source-side cascode element, the sink-side cascode element is operatively disposed between the current source and the current sink, the sink-side enable is operatively connected to the sink-side cascode element, the channel output is operatively connected between the current source and the current sink, the DC blocking capacitor is operatively connected to the channel output, the discharge switch is operatively disposed between the DC blocking capacitor, the current source, and the sink-side cascode element, the discharge enable is operatively connected to the discharge switch, and the channel output is operatively connected between the current source and the current sink.

In accordance with another aspect of the present disclosure, an electrical stimulation system is provided comprising an output pulse circuitry, a controller operatively connected to the output pulse circuitry, and a safety monitor operatively connected to the controller and the output pulse circuitry. The output pulse circuitry may comprise a plurality of output channel circuits operatively connected to a plurality of electrodes, wherein each output channel circuit is configured to deliver a stimulation pulse via an electrode of the plurality of electrodes. The controller can be configured to generate and deliver a stimulation pulse signal that will be used by the output pulse circuitry to generate the stimulation pulse, and to instruct at least one of the plurality of output channel circuits to deliver a stimulation pulse based on the stimulation pulse signal. Further, the safety monitor can include a plurality of error detection circuits and a stimulation disable logic circuit operatively connected to the plurality of error detection circuits, wherein the plurality of error detection circuits includes one or more of a first phase error detection circuit; a second phase error detection circuit; a third phase error detection circuit; a stimulation pulse rate error detection circuit; a first overlap error detection circuit; a second overlap error detection circuit; and a third overlap error detection circuit.

In accordance with a further aspect of the present disclosure, there is provided an output channel circuit for use in an electrical stimulation device that includes: a high-voltage domain comprising a channel output, a current source, a current mirror, a first resistor, and a second resistor; and a low-voltage domain comprising a reference current generator, a source-side amplitude control, a source-side cascode element, a current sink, a sink-side amplitude control, and a sink-side cascode element.

BRIEF DESCRIPTION OF THE DRAWINGS

The subject disclosure may take form in various components and arrangements of components, and in various steps and arrangement of steps. The drawings are only for purposes of illustrating the preferred embodiments and are not to be construed as limiting the subject disclosure.

DETAILED DESCRIPTION

Figure 1:
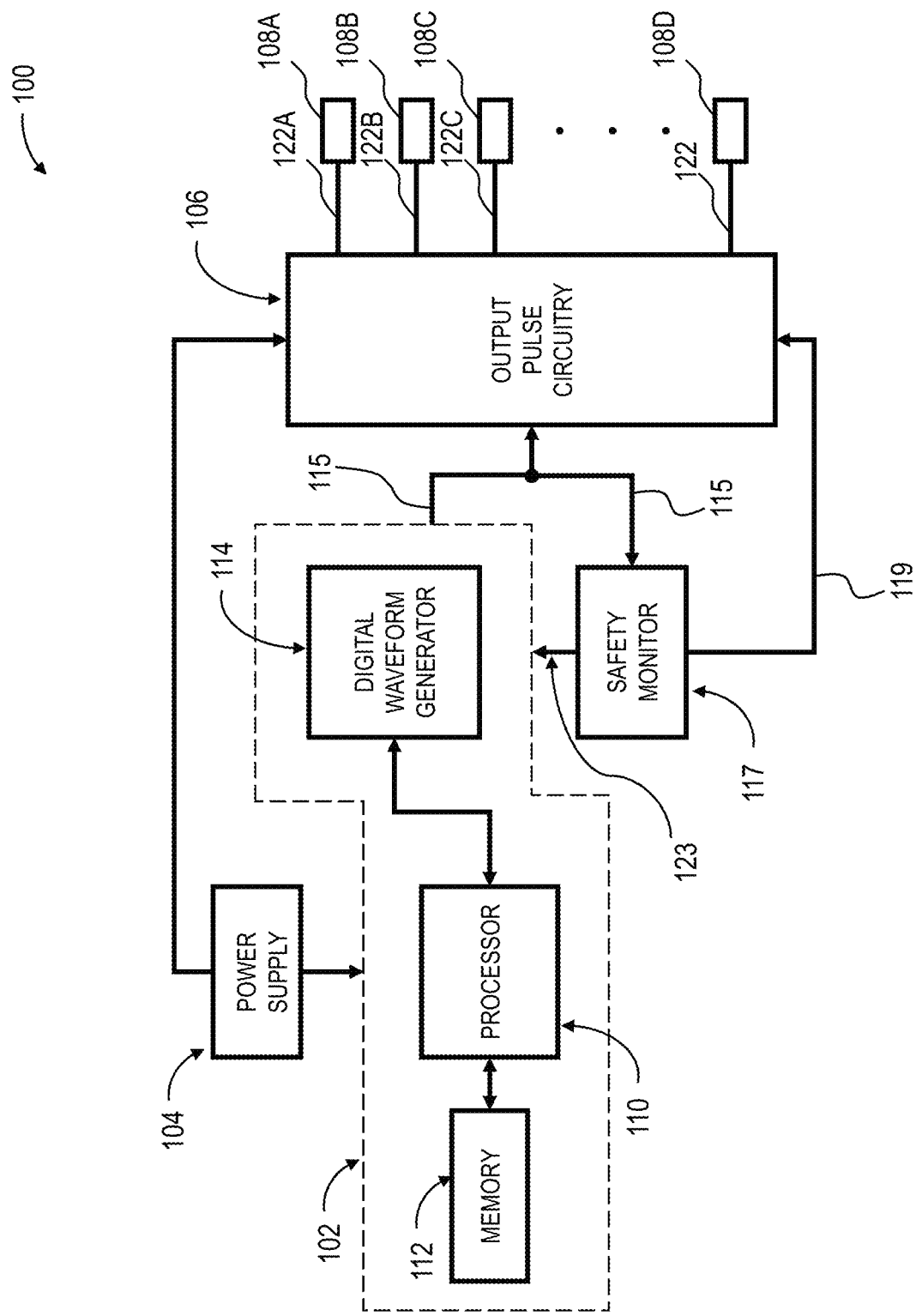
FIG. 1 is block diagram of an electrical stimulation system in accordance with one embodiment of the subject application.

The present disclosure may be understood more readily by reference to the following detailed description and the various drawings discussed therein. In accordance with one aspect, the high-voltage stimulation design of the subject application provides a high-voltage stimulator that is extremely portable, is readily scalable to include tens or hundreds of stimulation channels, can be scaled and easily tuned to specific voltages and currents for a variety of applications, and allows for any combination of channels to provide current simultaneously thereby allowing full current steering. Additionally, the high-voltage stimulators incorporating the output pulse circuitry of the subject application allow for independent control of the amplitude and polarity of each channel, and allow for all channels to be driven by a single waveform source, which is not limited to rectangular or trapezoidal profiles. That is, the architecture described herein allows for the stimulation of individual channels, including between any channel pair, which provides for additional stimulation and safety functionalities (i.e., customizable stimulation patterns, ESD diode checks, impedance checks, etc.).

In accordance with another aspect, a stimulation safety monitoring circuit of the subject application provides an architecture capable of detecting harmful timing faults that can occur due to a hardware or software error related to the clock source used to generate stimulation timing, detecting when stimulation pulse phases are skipped or performed out-of-order due to a hardware or software fault, and detecting when pulse phases are overlapping due to a hardware or software fault. Furthermore, the safety monitors of the subject application allow for the detection of cumulative errors that cannot be detected by other architectures, and do not require additional hardware as output channel counts increase.

According to one aspect, there is provided electrical stimulation devices and systems that includes the high-voltage output pulse circuitry disclosed herein, the stimulation monitoring architecture disclosed herein, or both.

In the following specification and the claims which follow, reference will be made to a number of terms which shall be defined to have the following meanings.

Definitions

In the following specification and the claims that follow, reference will be made to a number of terms which shall be defined to have the following meanings. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." More specifically, the term "about" may refer to plus or minus 10% of the indicated number.

High-Voltage Stimulation Devices

Turning now to FIG. 1, there is shown a block diagram of an electrical stimulation system 100 in accordance with one exemplary embodiment of the subject application. The system 100 includes a controller 102, a power supply 104, an output pulse circuitry 106 operatively connected to the power supply 104, and a plurality of electrodes 108A, 108B, 108C, 108D operatively connected to the output pulse circuitry 106. The controller 102 is operatively connected to the output pulse circuitry 106, and can be configured to instruct the output pulse circuitry to deliver an electrical output pulse via one or more of the plurality of electrodes 108A, 108B, 108C, 108D. That is, the controller 102 can be configured to generate and send a stimulation pulse signal to the output pulse circuitry 106, and the output pulse circuitry 106 can be configured to generate an output pulse based on the stimulation pulse signal. As discussed below, the stimulation pulse signal may include multiple phases, including a first phase (i.e. stimulation phase), a second phase (i.e. a charge-balancing phase), and a third phase (i.e. a charge balance correction phase). Further, the electrodes 108A, 108B, 108C, 108D can be positioned adjacent to and in contact with an outer surface of a patient's body, and the system 100 delivers electrical stimulation based on the stimulation pulse signal via the electrodes 108A, 108B, 108C, 108D to the patient's tissues (e.g. muscles or nerves) in the region of that outer surface.

In particular embodiments, the power supply 104 connected to the output pulse circuitry 106 is a high-voltage power supply 104. In some embodiments, the maximum voltage supplied by the power supply 104 to the output pulse circuitry 106 is at least 20 volts, or at least 50 volts, or at least 100 volts, or at least 150 volts, or at least 200 volts, or at least 250 volts, or at least 300 volts, or at least 350 volts, or at least 400 volts, or at least 500 volts, or at least 1000 volts, or other suitable voltages therebetween. In other embodiments, the maximum voltage supplied by the power supply 104 to the output pulse circuitry 106 is from about 20 to about 1000 volts, from about 100 to about 1000 volts, from about 150 to about 500 volts, from about 200 to about 500 volts, from about 250 to about 500 volts, from about 300 to about 500 volts, or from about 350 to about 500 volts, or from about 400 to about 500 volts, or from about 450 to about 500 volts, or other suitable voltages therebetween.

The controller 102 may be connected to the power supply 104, or may be connected to a second power supply (not shown). In particular embodiments, the controller 102 comprises a processor 110 operatively connected to a memory 112 containing programming instructions that are configured to generate a desired electrical stimulation pattern or sequence, and to instruct the output pulse circuitry to deliver such electrical output pulse(s). In particular, the controller 102 may contain a digital waveform generator 114, which instructs the output pulse circuitry 106 to deliver a desired output pulse based on a variety of parameters 115 (discussed below) via the electrodes 108A, 108B, 108C, 108D. The controller 102 may be variously embodied, such as by one or more microcontrollers.

The system 100 further includes a stimulation safety monitoring circuit (i.e. safety monitor) 117 operatively connected to the controller and the output pulse circuitry. The safety monitor 117 may receive as inputs one or more of a plurality of parameters 115, from the controller 102, which determines the output stimulation pulses generated by the output pulse circuitry 106 and delivered by the electrodes 108A, 108B, 108C, 108D. In particular embodiments, the safety monitor 117 may output a stimulation disable signal 119 to the output pulse circuitry 106, which prevents the system 100 from delivering potentially harmful stimulation pulses. The safety monitor 117 may also output one or more error detection signals 123, which may be received and used by the controller 102 to adjust or update the electrical stimulation program.

The system 100 may also include a plurality of leads 122A, 122B, 122C, 122D that connect the output channels of the output pulse circuitry 106 (see FIG. 2) to a corresponding electrode 108A, 108B, 108C, 108D.

Figure 12:
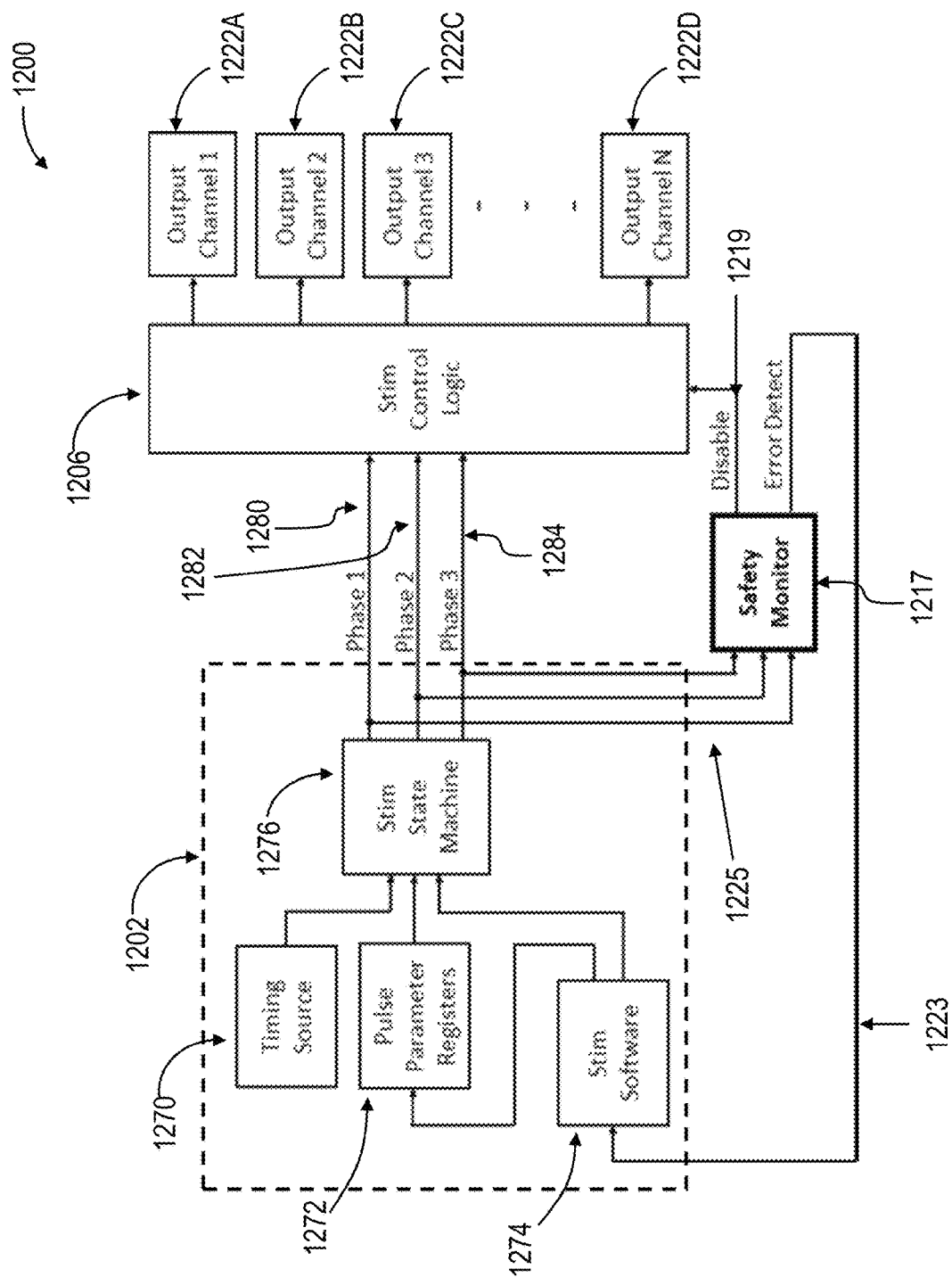
FIG. 12 is a second block diagram of an electrical stimulation system incorporating a safety monitory in accordance with one embodiment of the subject application.

In various embodiments, the system 100 may also include other components, such as, for example, a timing source for controlling stimulation pulse width and pulse rate, pulse parameter registers that contain pulse parameter information, or a stimulation state machine for driving the pulse control logic (see FIG. 12).

Figure 2:
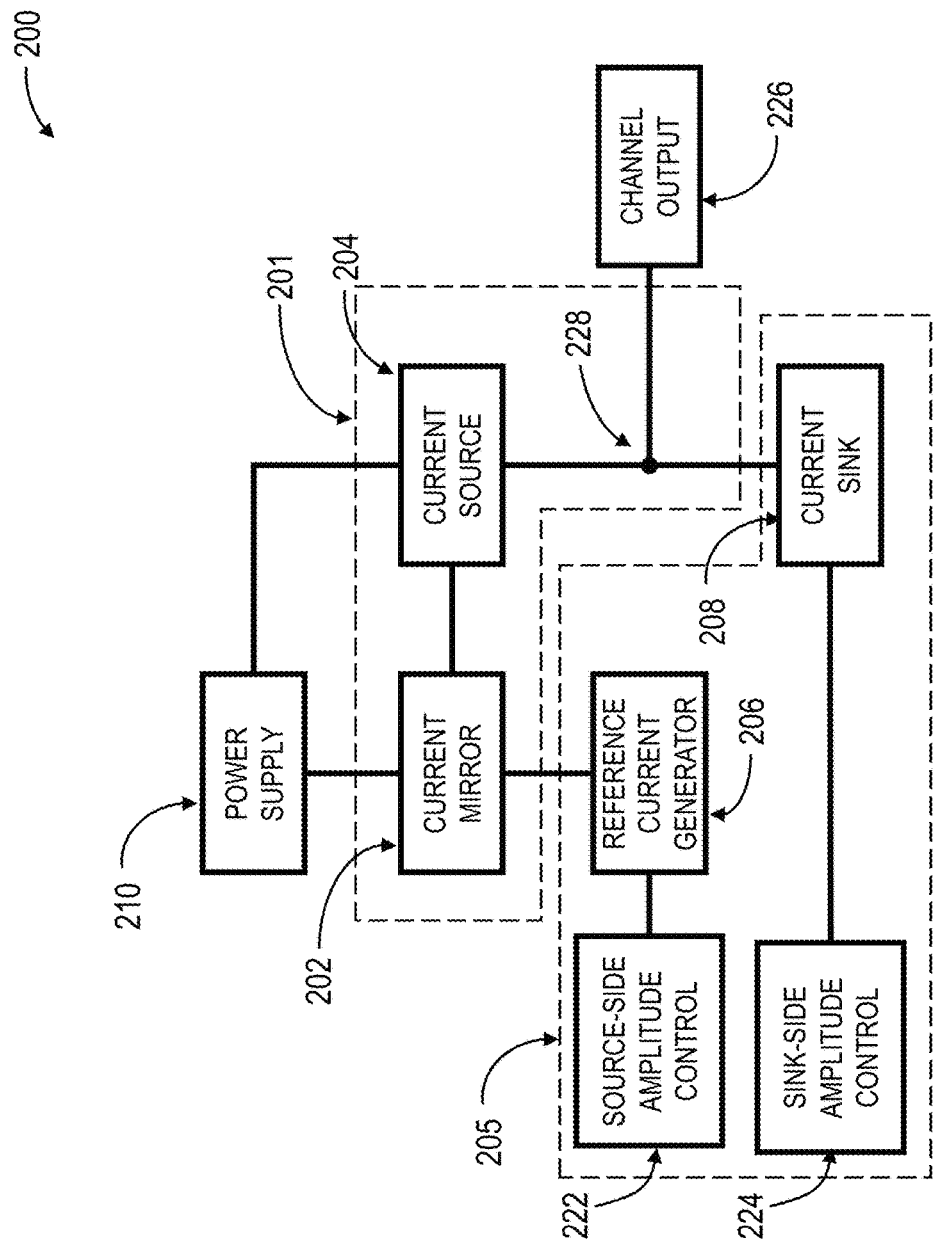
FIG. 2 is a block diagram of an electrical stimulation circuit in accordance with one embodiment of the subject application.

Turning now to FIG. 2, there is shown a block diagram of a single output channel circuit 200 contained within the output pulse circuitry 106 in accordance with one aspect of this disclosure. The output channel circuit 200 includes a high-voltage domain 201 and a low-voltage domain 205. The high-voltage domain 201 may comprise a current source 204 operatively connected to the high-voltage power supply 210, a current mirror 202 operatively connected to the current source 204 and the high-voltage power supply 210. The current source 204 limits the current that can flow from the high-voltage power supply 210, and the current mirror 202 is connected to the current source 204 in order to control the amplitude of the output current (i.e. current delivered through the channel output 226).

The low-voltage domain 205 may comprise a reference current generator 206 operatively connected to the current mirror 202, a source-side amplitude control 222 operatively connected to the reference current generator 206, a current sink 208 operatively connected to the current source 204, and a sink-side amplitude control 224 operatively connected to the current sink 208. The reference current generator 206 determines how much current is pulled through the current mirror 202, which in turn determines the output current provided by the current source 204. In particular embodiments, a first reference voltage is supplied by the source-side amplitude control 222 to the reference current generator 206, thereby pulling a corresponding current through the current mirror 202. As a result, the current source 204 provides a current to the output channel 226 that corresponds to the current pulled through the current mirror 202.

Although the output channel circuit 200 shown in FIG. 2 includes a current source 204 and a current sink 208, it is contemplated that each channel circuit 200 may comprise only one of a current source 204 and a current sink 208. In other words, the channel circuit 200 may not include the current source 204 or current sink 208. In such embodiments, each channel circuit 200 may instead be connected to a passive correction circuit.

In some embodiments, the maximum output current at the channel output 226 is from about 3 mA to 100 mA. In particular embodiments, the maximum output current at the channel output 226 is about 3 mA, or about 5 mA, or about 10 mA, or about 12 mA, or about 15 mA, or about 20 mA, or other suitable amperages therebetween.

In particular embodiments, a second reference voltage is supplied by the sink-side amplitude control 224 to the current sink 208. The second reference voltage produces a current through the current sink 208, which in turn sinks current from the channel output 226.

In particular embodiments, the source-side amplitude control 222 and the sink-side amplitude control 224 may operate at low and very low voltages. For example, the source-side amplitude control 222 and the sink-side amplitude control 224 may operate at a digital voltage of less than about 5 volts, or less than about 3.3 volts, or less than about 2.5 volts, or less than about 1.8 volts. In some embodiments, the source-side amplitude control 222 and the sink-side amplitude control 224 may operate at a digital voltage of from about 1.8 volts to about 5 volts, or from about 2.5 volts to about 3.3 volts. In specific embodiments, the source-side amplitude control 222 and the sink-side amplitude control 224 may operate at a digital voltage of about 2.5 volts, or about 3.3 volts.

The output channel circuit 200 also includes a channel output 226, operatively connected to a terminal 228 between the current source 204 and the current sink 208. The output channel 226 outputs an output current from the pulse generating output stage (i.e. output channel circuit) 200. In particular embodiments, the channel output 226 may include an electrostatic discharge (ESD) diode (not shown) to further protect from overvoltage conditions.

In addition to being able to provide constantly controlled current to the output channel, the output channel circuits 200 disclosed herein reduce the overall footprint of the output pulse circuitry 106 by minimizing the number of circuit components in the high-voltage domain 201. More specifically, only the components in the high-voltage domain 201 must have a high voltage rating, whereas the components in the low-voltage domain 205 do not require high voltage ratings. For example, each of the components in the high-voltage domain 201 may have a voltage rating of about 20 V to about 1000 V, including from about 100 V to 1000 V and from about 150 V to about 500 V. In contrast, each of the components in the low-voltage domain 205 may have a voltage rating of about 1.8 V to about 50 V, including from about 5.5 V to about 10 V.

With reference to both FIG. 1 and FIG. 2, the output channel circuits 200 that comprise output pulse circuitry 106 can operate over a wide range of voltages and can be scaled to a high number of stimulation channels 200. For example, in some embodiments, the high-voltage power supply 104 can be scaled to operate at voltages from about 20 volts to about 1000 volts, or from about 50 volts to about 200 volts. [BJG1][AN2] In further embodiments, the system 100 may include from about 10 to about 1000 output channel circuits 200 (i.e. from about 10 to about 1000 output channels 226). In specific embodiments, the system 100 may include at least 50 output channel circuits 200, or at least 60 output channel circuits 200, or at least 70 output channel circuits 200, or at least 80 output channel circuits 200, or at least 90 output channel circuits 200, or at least 100 output channel circuits 200, or at least 110 output channel circuits 200, or at least 120 output channel circuits 200, or at least 130 output channel circuits 200, or at least 140 output channel circuits 200, or at least 150 output channel circuits 200, or at least 160 output channel circuits 200, or at least 170 output channel circuits 200, or at least 180 output channel circuits 200, or at least 190 output channel circuits 200, or at least 200 output channel circuits 200, or at least 250 output channel circuits 200, or at least 300 output channel circuits 200, or at least 350 output channel circuits 200, or at least 400 output channel circuits 200, or at least 450 output channel circuits 200, or at least 500 output channel circuits 200, or at least 600 output channel circuits 200, or at least 700 output channel circuits 200, or at least 800 output channel circuits 200, or at least 900 output channel circuits 200, or at least 1000 output channel circuits 200. In some embodiments, the power supply 210 may be a single circuit that is shared by all output channel circuits 200, while in other embodiments, an independent power supply 210 may be included with each output channel circuit 200.

Turning now to FIGS. 3-7, various embodiments of the output channel circuit 200 are illustrated.

Figure 3:
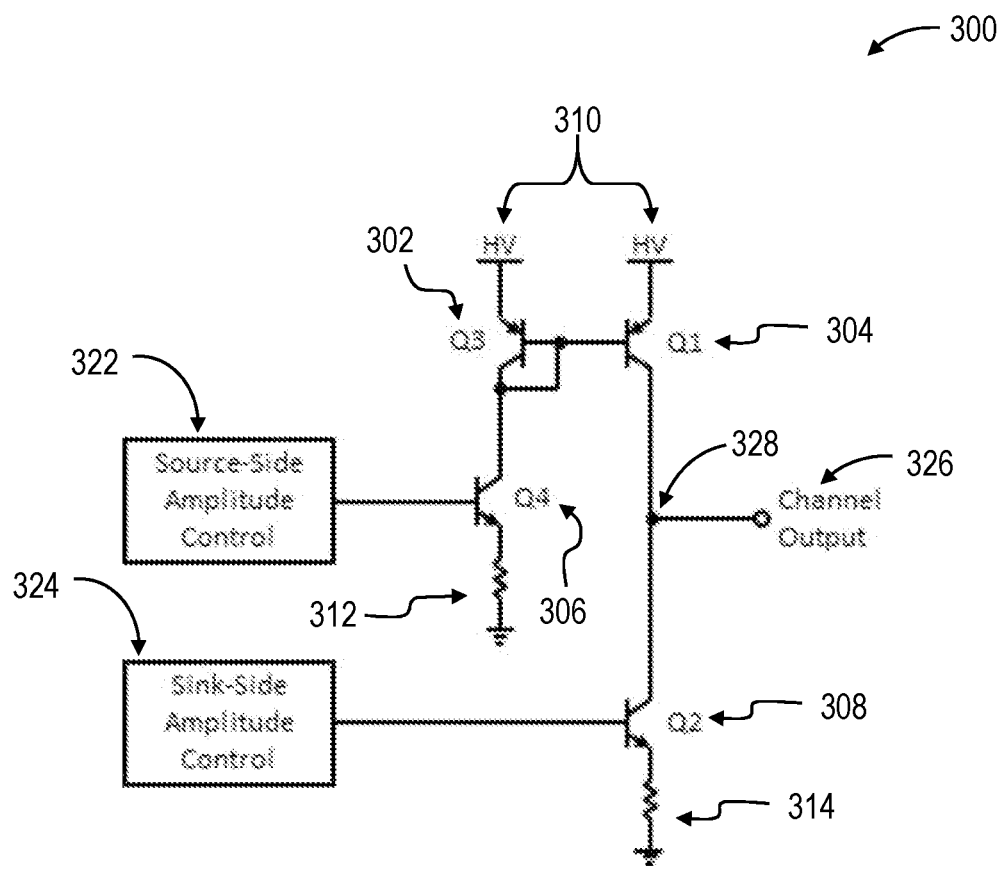
FIG. 3 is a circuit diagram of an electrical stimulation circuit in accordance with one embodiment of the subject application.

With reference to FIG. 3, a first embodiment of the output channel circuit 300 is shown. As shown, the current mirror 302, the current source 304, the reference current generator 306, and the current sink 308 can be transistors. In particular embodiments, the output channel circuit 300 may comprise a combination of NPN and PNP transistors. For example, in some embodiments, the current mirror 302 and the current source 304 may be PNP transistors. In further embodiments, the reference current generator 306 and the current sink 308 can be NPN transistors. The emitter terminal of the current mirror 302 and the emitter terminal of the current source 304 may be connected to a voltage supply 310, such as a high-voltage power supply 310. Further, the collector terminals of the current mirror 302 and current source 304 may be connected to a terminal of the reference current generator 306 and current sink 308, respectively. The emitter terminals of the reference current generator 306 and the current sink 308 may be connected to ground through current-limiting resistors 312, 314.

In particular embodiments, the base terminal of the current mirror 302 is connected to the base terminal of the current source 304 and the collector terminals of the current mirror 302 and reference current generator 306 at a terminal 320.

The source-side amplitude control 322 and the sink-side amplitude control 324 may be connected to the base terminals of the reference current generator 306 and the current sink 308, respectively. In particular embodiments, the source-side amplitude control 322 and the sink-side amplitude control 324 provide signals to the reference current generator 306 and the current sink 308, respectively, which control the electrical output pulse to be delivered via the output channel 326. In particular embodiments, the output channel 326 can be connected to the current source 304 and the current sink 308. For example, the output channel 326 may be connected at a terminal 328.

In particular embodiments, the transistors 302, 304, 306, 308 may have a voltage rating of about 20 V to about 1000 V, including from about 150 V to about 500 V. In some embodiments, the source-side amplitude control 322 and the sink-side amplitude control 324 may have a voltage rating of about 1.8 V to about 50 V, including from about 1.8 V to about 20 V and from about 1.8 V to about 5.0 V. In further embodiments, a low-voltage domain of the circuit 300 includes one or more of: the reference current generator 306; current sink 308; the source-side amplitude control 322; and the sink-side amplitude control 324. In still further embodiments, a high-voltage domain of the circuit 300 may include at least the current mirror 302 and the current source 304.

Figure 4:
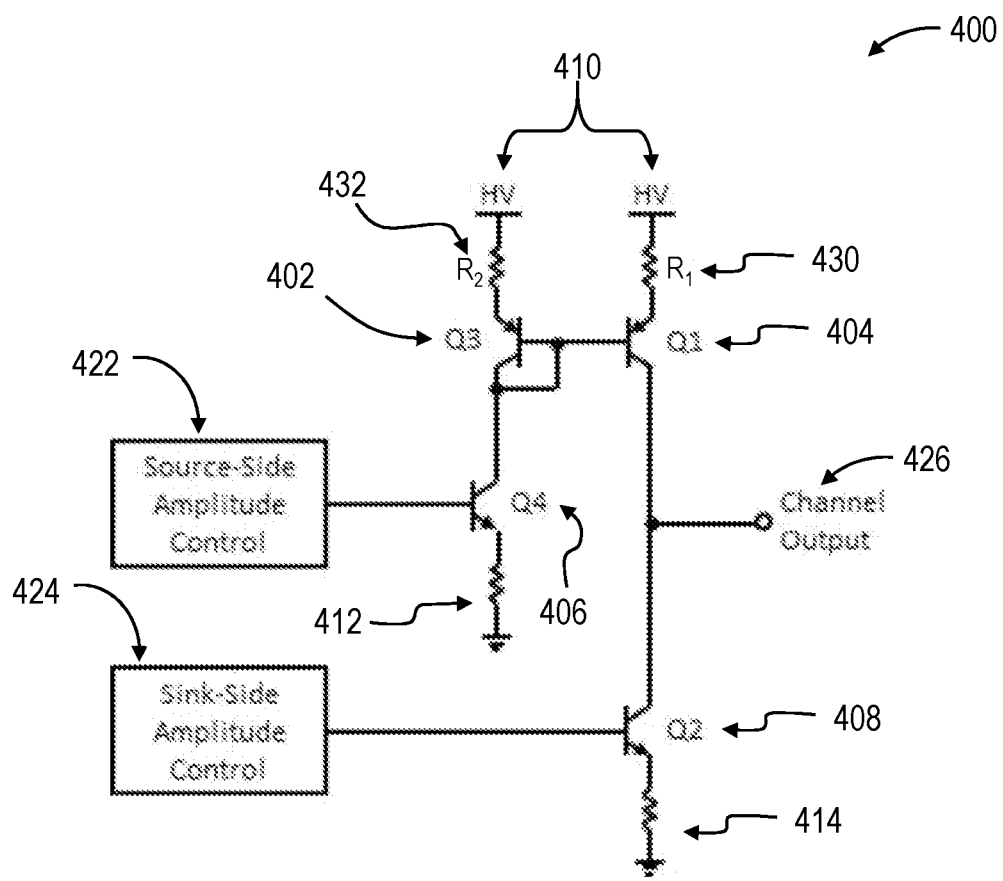
FIG. 4 is a circuit diagram of an electrical stimulation circuit in accordance with a second embodiment of the subject application.

With reference to FIG. 4, a second embodiment of the output channel circuit 400 is shown. As illustrated, an output channel circuit 400 may comprise a current mirror 402, a current source 404, a reference current generator 406, a current sink 408, a source-side amplitude control 422, a sink-side amplitude control 424, and a channel output 426. The reference current generator 406 and the current sink 408 may be connected to current-limiting resistors 412, 414 respectively, which are connected to ground.

Additionally, in particular embodiments, the circuit 400 may include a first resistor 430 operatively connected between the high-voltage power supply 410 and the current source 404, and a second resistor 432 operatively connected between the high-voltage power supply 410 and the current mirror 402. The first resistor 432 can have a first resistance ($R_1$), and the second resistor 430 can have a second resistance ($R_2$). In some embodiments, the first and second resistors 430, 432 may comprise one or more resistors, wherein the first resistance $R_1$ is the sum of the resistors comprising the first resistor 430 and the second resistance $R_2$ is the sum of the resistors comprising the second resistor 432.

The second resistance $R_2$ may be greater than the first resistance $R_1$. For example, the second resistance may be at least 2 to 5 times greater than the first resistance, or at least 5 to 10 times greater than the first resistance, or at least 10 to 20 times greater than the first resistance, or at least 20 to 50 times greater than the first resistance, or at least 50 to 100 times greater than the first resistance.

Further, the first and second resistors 430, 432 may have a voltage rating of 150 V to 500 V. In particular embodiments, the high-voltage domain may include the first and second resistors 430, 432.

Figure 5:
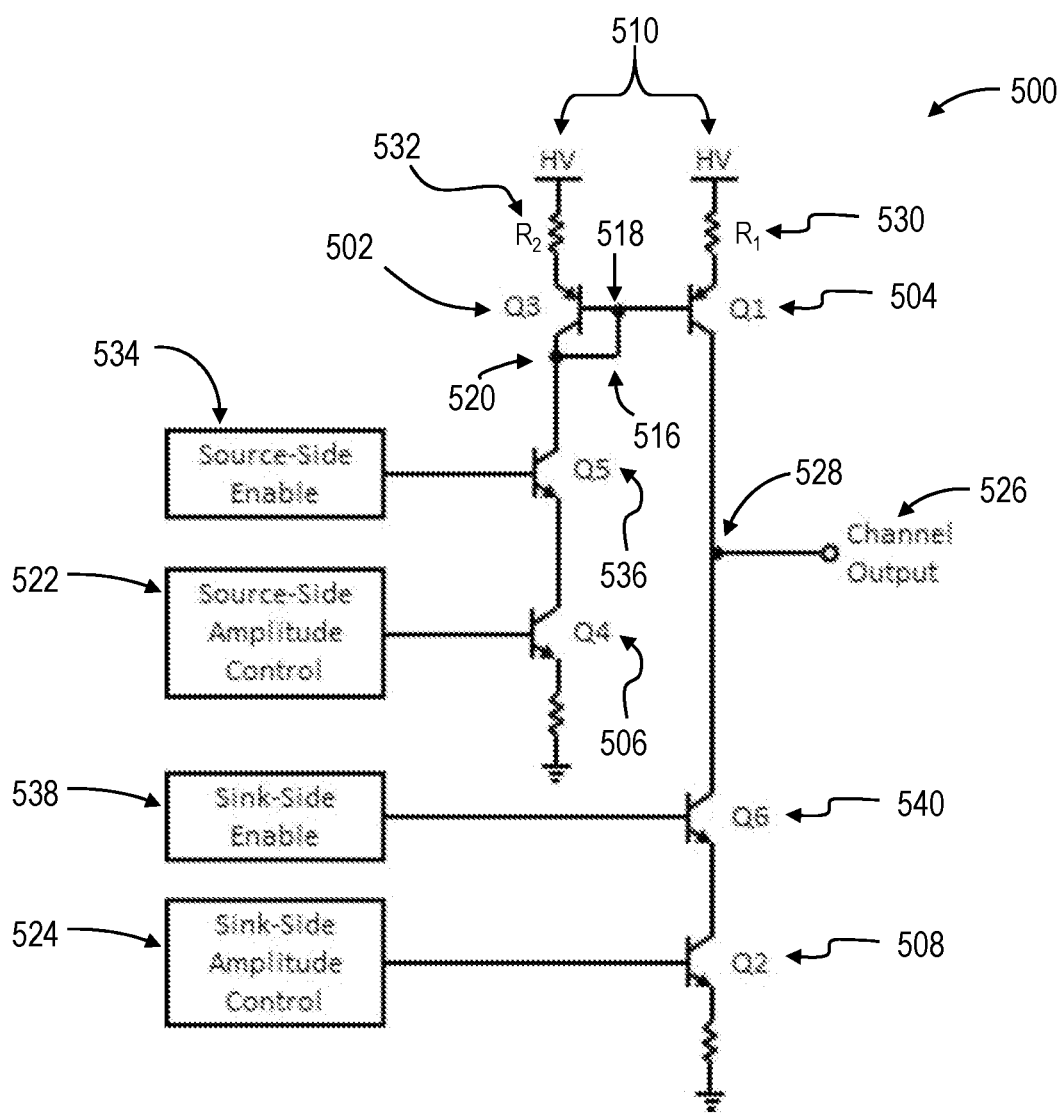
FIG. 5 is a circuit diagram of an electrical stimulation circuit in accordance with a third embodiment of the subject application.

Turning now to FIG. 5, another embodiment of the output channel circuit 500 is shown. Like the circuit 400 shown in FIG. 4, the output channel 500 includes a high-voltage power supply 510, a current mirror 502, a current source 504, a first resistor 530, a second resistor 532, a reference current generator 506, a current sink 508, a source-side amplitude control 522, a sink-side amplitude control 524, and a channel output 526. Additionally, the output channel circuit 500 may further comprise a source-side enable 534 operatively connected to a source-side cascode element 536, and a sink-side enable 538 operatively connected to a sink-side cascode element 540. In such embodiments, the source-side cascode element 536 may be operatively connected to the current mirror 502 and the reference current generator 506, while the sink-side cascode element 540 may be operatively connected to the current source 504 and the current sink 508. In particular embodiments, the source-side cascode element 536 and the sink-side cascode element 540 may be transistors, such as, for example, NPN type transistors. The emitter terminal and the collector terminal of the source-side cascode element 536 may be connected to the collector terminal of the reference current generator 506 and the collector terminal of the current mirror 502, respectively. Similarly, the emitter terminal and the collector terminal of the sink-side cascode element 540 may be connected to the collector terminal of the current sink 508 and the collector terminal of the current source 504, respectively.

The circuit 500 also includes a connector 516 connecting the base terminals of the current mirror 502 and the current source 504 at a terminal 518 to the collector terminals of the current mirror 502 and the source-side cascode element 536 at a terminal 520. Further, the channel output 526 may be operatively connected to the current source 504 and the sink-side cascode element 540, for example, at a terminal 528.

Figure 6:
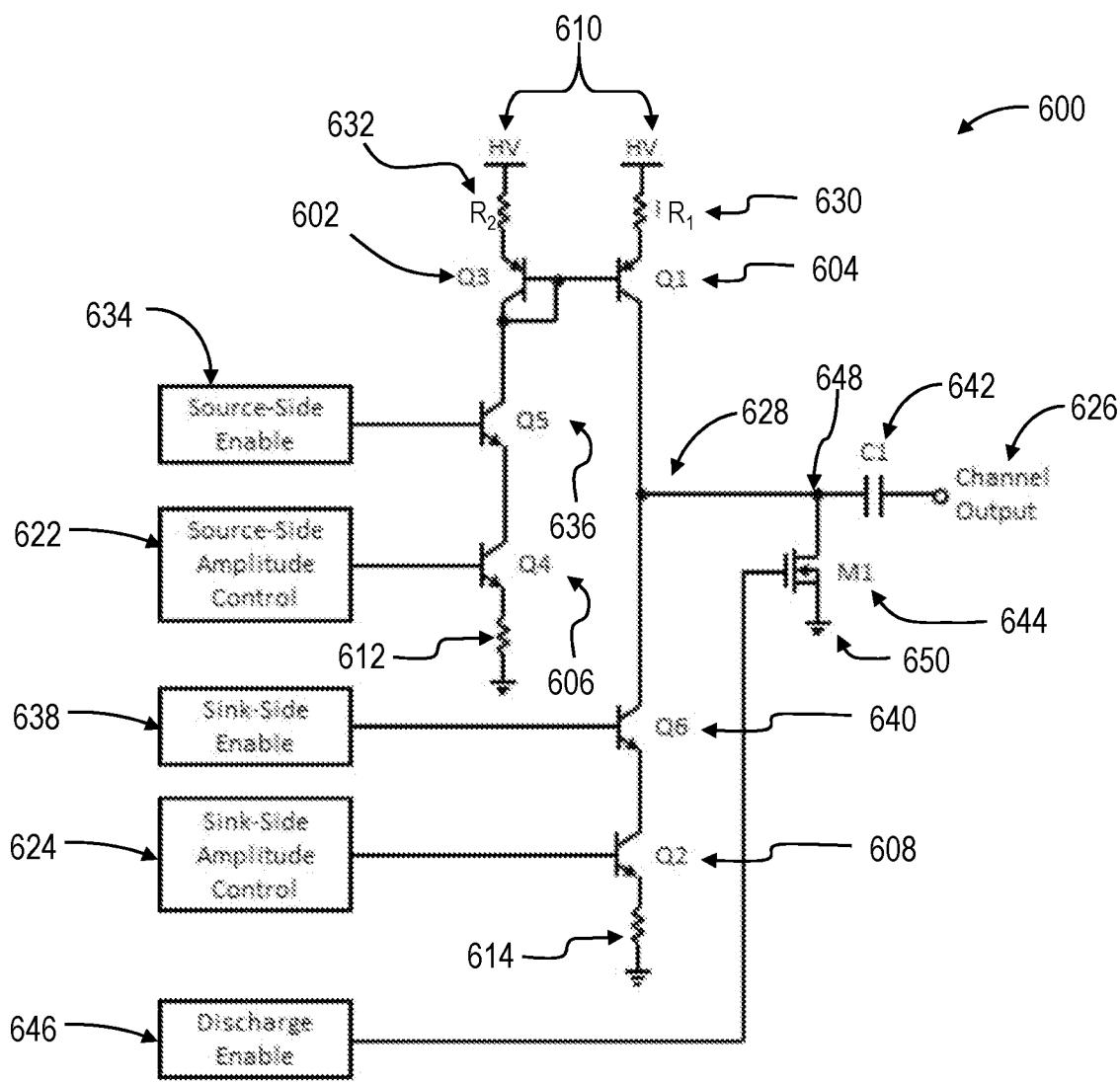
FIG. 6 is a circuit diagram of an electrical stimulation circuit in accordance with another embodiment of the subject application.

Turning to FIG. 6, another embodiment of the output channel circuit 600 is provided, which includes: a high-voltage power supply 610 operatively connected to a first resistor 630 and a second resistor 632, a current mirror 602 operatively connected to the second resistor 632 and a source-side cascode element 636, a current source 604 operatively connected to the first resistor 630 and a sink-side cascode element 640, a reference current generator 606 operatively connected to the source-side cascode element 636 and a current-limiting resistor 612 connected to ground, a current sink 608 operatively connected to the sink-side cascode element 640 and a current-limiting resistor 614 connected to ground, a source-side enable 634 operatively connected to the source-side cascode element 636, a source-side amplitude control 622 operatively connected to the reference current generator 606, a sink-side enable 638 operatively connected to the sink-side cascode element 640, a sink-side amplitude control 624 operatively connected to the current sink 608, and a channel output 626.

The circuit 600 may further include a DC blocking capacitor 642, a discharge switch 644, and a discharge enable 646. DC blocking capacitor 642 may be operatively connected to the channel output 626, and the discharge switch 644 may be operatively connected to the DC blocking capacitor 642, the current source 604, and the sink-side cascode element 640 at terminals 648, 628. The discharge switch 644 may further be connected to the discharge enable 646. In particular embodiments, the discharge switch 644 is an NPN type transistor, wherein the discharge enable 646 is connected to the base terminal of the switch 644, the emitter terminal in connected to a ground 650, and the collector terminal is connected to the terminal 648. In specific embodiments, the discharge switch 644 may be a bipolar junction transistor (BJT) or a field effect transistor (FET), such as an N-channel BJT or an N-channel FET.

In some embodiments, the DC blocking capacitor 642 can have a capacitance of about 0.1 µF to about 100 µF. In certain embodiments, the DC blocking capacitor 642 may include one or more individual capacitors operatively connected in series or in parallel to provide the desired capacitance. For example, in one specific embodiment, the DC blocking capacitor 642 may be two capacitors connected in series, each with a 4.7 µF capacitance and a voltage rating of 100 V. Further, the DC blocking capacitor 642 and the discharge switch 644 can have a voltage rating of about 20 V to about 1000 V, including from about 100 V to about 500 V. In particular embodiments, the high-voltage domain may include one or both of the DC blocking capacitor 642 and the discharge switch 644.

Figure 7:
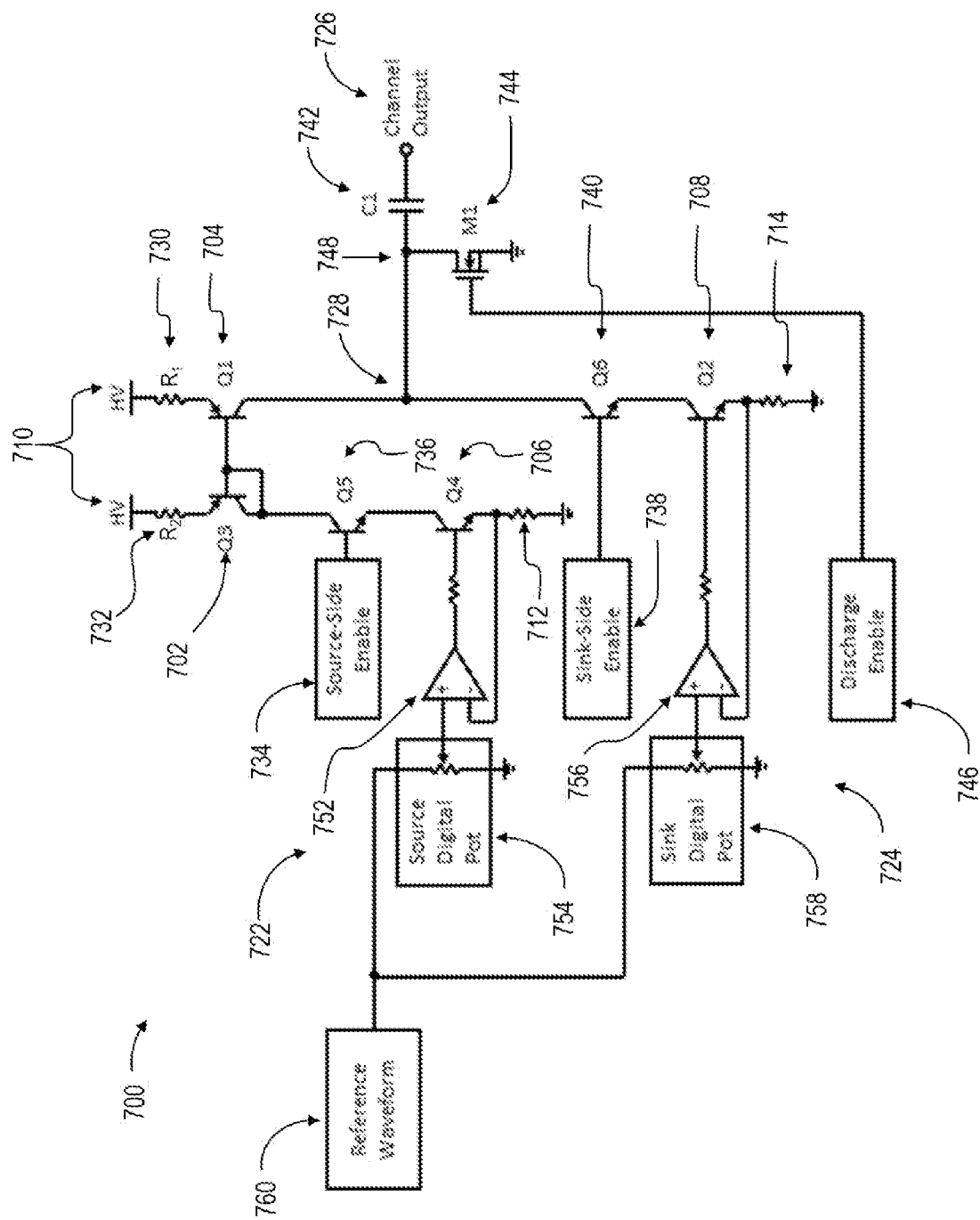
FIG. 7 is a circuit diagram of an electrical stimulation circuit in accordance with still another embodiment of the subject application.

Turning to FIG. 7, another embodiment of the output channel circuit 700 is provided, which includes: a high-voltage power supply 710 operatively connected to a first resistor 730 and a second resistor 732, a current mirror 702 operatively connected to the second resistor 732 and a source-side cascode element 736, a current source 704 operatively connected to the first resistor 730 and a sink-side cascode element 740, a current sink 708 operatively connected to the sink-side cascode element 740 and a current limiting resistor 714 connected to ground, a source-side enable 734 operatively connected to the source-side cascode element 736, a sink-side enable 738 operatively connected to the sink-side cascode element 740, a reference current generator 706 operatively connected to the source-side cascode element 736 and a current limiting resistor 712 connected to ground, a channel output 726, a DC blocking capacitor 742 operatively connected to the channel output 726, a discharge switch 744 operatively connected to the DC blocking capacitor 742, the current source 704, and the sink-side cascode element 740 at terminals 748, 728, and a discharge enable 746 operatively connected to the discharge switch 744.

The output channel circuit 700 also includes a source-side amplitude control 722 operatively connected to the reference current generator 706, and a sink-side amplitude control 724 operatively connected to the current sink 708. In particular embodiments, the source-side amplitude control 722 comprises a source-side operational amplifier 752 operatively connected to the reference current generator 706, and a source digital potentiometer 754 operatively connected to the source-side operational amplifier 752. Similarly, the sink-side amplitude control 724 can comprise a sink-side operational amplifier 756 operatively connected to the current sink 708, and a sink-side digital potentiometer 758 operatively connected to the sink-side operational amplifier 756. In particular embodiments, the wiper output of the potentiometers 754, 758 are connected to the non-inverting input of the operational amplifiers 752, 756, respectively. In further embodiments, the emitter terminal output of the reference current generator 706 is connected to the inverting input of the operational amplifier 752, and the emitter terminal output of the current sink 708 is connected to the inverting input of the operational amplifier 756.

In preferred embodiments, the source-side amplitude control 722 and sink-side amplitude control 724 are operatively connected to a reference waveform generator 760. For example, as illustrated in FIG. 7, a reference waveform generator 760 is operatively connected to the source-side potentiometer 754 and the sink-side potentiometer 758. The reference waveform generator 760 can be configured to generate a reference waveform signal, which can be provided to both the reference current generator 706 and current sink 708 of the circuit 700 via the source-side amplitude control 722 and the sink-side amplitude control 724, respectively. In other words, the reference waveform signal may be provided to both the source-side potentiometer 754 and the sink-side potentiometer 758, which in turn controls the source and sink of the output channel circuit 700.

The digital potentiometers 754, 758 control the amplitudes of the source and sink (discussed further below), and can be independently programmable to allow the source and sink amplitudes to be set to different values. The digital potentiometers 754, 758 can be programmed prior to the start of an output pulse, whereas the reference waveform generator 760, source-side enable 734, sink-side enable 738, and discharge enable 746 may be driven during the sourcing and sinking of an output pulse. In some embodiments, the reference waveform generator 760 may be, for example, a digital-to-analog converter, or may be any other type of waveform generator circuit.

With reference to FIGS. 1-7, the output pulse circuitry 106 may include the reference waveform generator 760 and a plurality of output channel circuits 200, 300, 400, 500, 600, 700. In particular embodiments, the controller 102 is configured to provide digital signals to at least one of the source-side enable 534, 634, 734, the sink-side enable 538, 638, 738, the source-side amplitude control 222, 322, 422, 522, 622, 722, the sink-side amplitude control 224, 324, 424, 524, 624, 724, and the discharge enable 646, 746. That is, the source-side enable 534, 634, 734, the sink-side enable 538, 638, 738, the source-side amplitude control 222, 322, 422, 522, 622, 722, the sink-side amplitude control 224, 324, 424, 524, 624, 724, and the discharge enable 646, 746 may be configured to receive digital signals from the controller 102.

In particular embodiments, the digital signals may include a digital source-side enable signal, a digital sink-side enable signal, and a digital discharge enable signal. The source-side enable 534, 634, 734 can be configured to receive the digital source-side enable signal from the controller 102. The sink-side enable 538, 638, 738 can be configured to receive the digital sink-side enable signal from the controller 102. The discharge enable 646, 746 can be configured to receive the digital discharge enable signal from the controller 102.

In further embodiments, the reference waveform generator 760 can be operatively connected to one or more of the plurality of output channel circuits 200, 300, 400, 500, 600, 700. The digital signals provided by the controller 102 can further include a digital reference waveform. That is, the reference waveform generator 760 can be configured to receive, from the controller 102, a digital reference waveform.

The digital signals provided by the controller 102 can be used by the plurality of output channel circuits 200, 300, 400, 500, 600, 700 to generate electrical output pulses. For example, the source-side enable 534, 634, 734 can provide a source-side enable signal to the source-side cascode element 536, 636, 736 based on the digital source-side enable signal received. Similarly, the sink-side enable 538, 638, 738 can provide a sink-side enable signal to the sink-side cascode element 540, 640, 740 based on the digital sink-side enable signal received. Further, the discharge enable 646, 746 can provide a discharge enable signal to the discharge switch 644, 744 based on the digital discharge enable signal received. Further, the source-side enable signal, the sink-side enable signal, and discharge enable signal may be logic-level signals and operate to prevent transient currents. In particular embodiments, one or more of the source-side enable signal, the sink-side enable signal, and the discharge enable signal may be a voltage of 1.8 V to 5 V.

In further embodiments, the reference waveform generator 760 can be connected to the source-side amplitude control 222, 322, 422, 522, 622, 722 and the sink-side amplitude control 224, 324, 424, 524, 624, 724 of one or more output channel circuits 200, 300, 400, 500, 600, 700, and can provide a reference waveform signal to the source-side amplitude control 222, 322, 422, 522, 622, 722 and the sink-side amplitude control 224, 324, 424, 524, 624, 724 based on the digital reference waveform signal received from the controller 102. In some embodiments, the same digital reference waveform is received by the waveform generator 760, and the reference waveform generator 760 provides a correspondingly similar or identical reference waveform signal that drives the electrical output pulse of one or more output channel circuits 200, 300, 400, 500, 600, 700, including a plurality of output channel circuits 200, 300, 400, 500, 600, 700. In particular, the plurality of output channel circuits 200, 300, 400, 500, 600, 700 may include from about 2 to about 10 output channel circuits 200, 300, 400, 500, 600, 700. In particular embodiments, the reference waveform signal can be provided to up to about 100% of the total number of output channel circuits 200, 300, 400, 500, 600, 700. That is, the reference waveform signal may be provided to all of the output channel circuits 200, 300, 400, 500, 600, 700.

Figure 8:
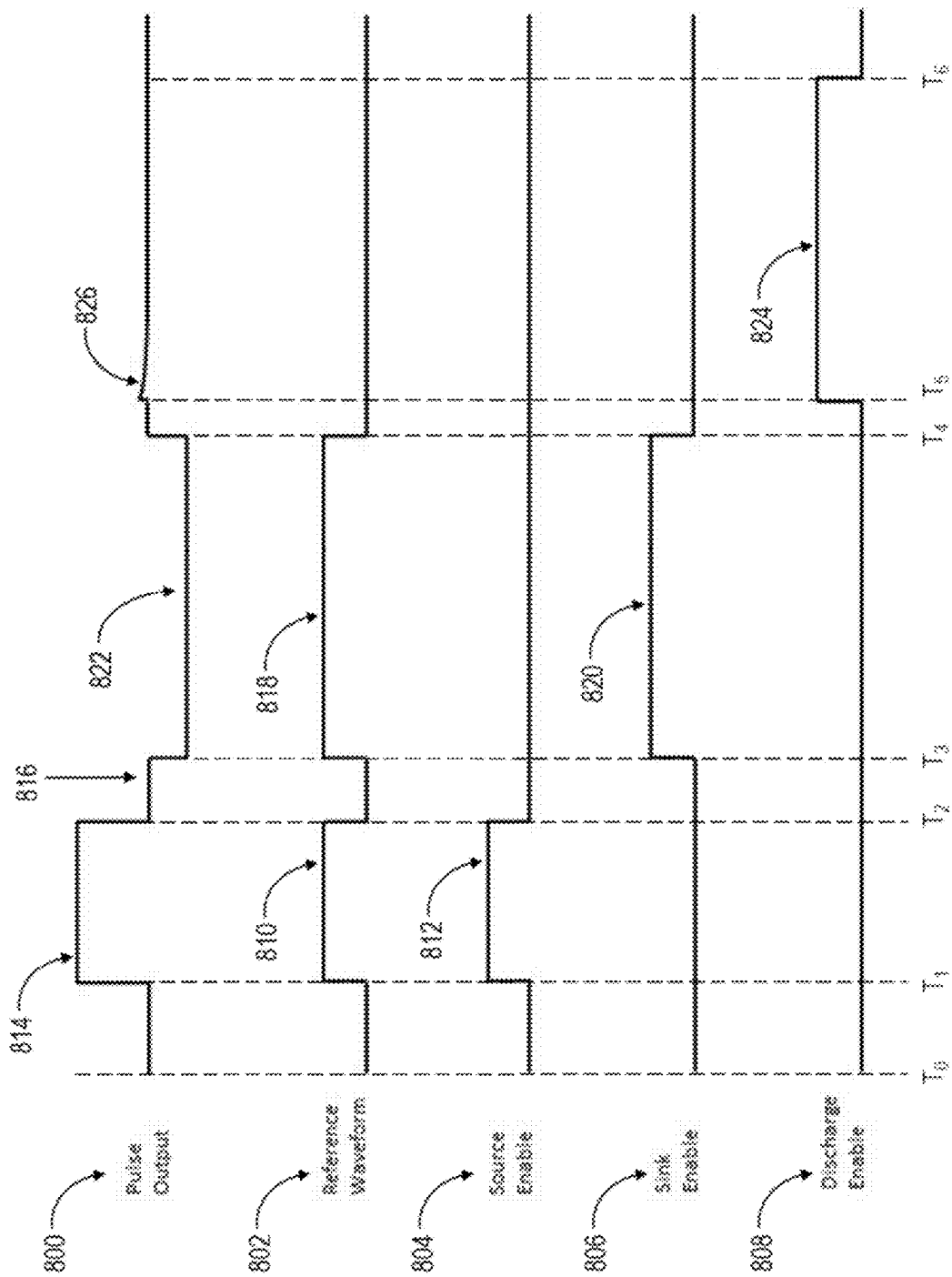
FIG. 8 is an example of an electrical stimulation pulse output and the underlying signals used to form the pulse output in accordance with one embodiment of the subject application.
Figure 9:
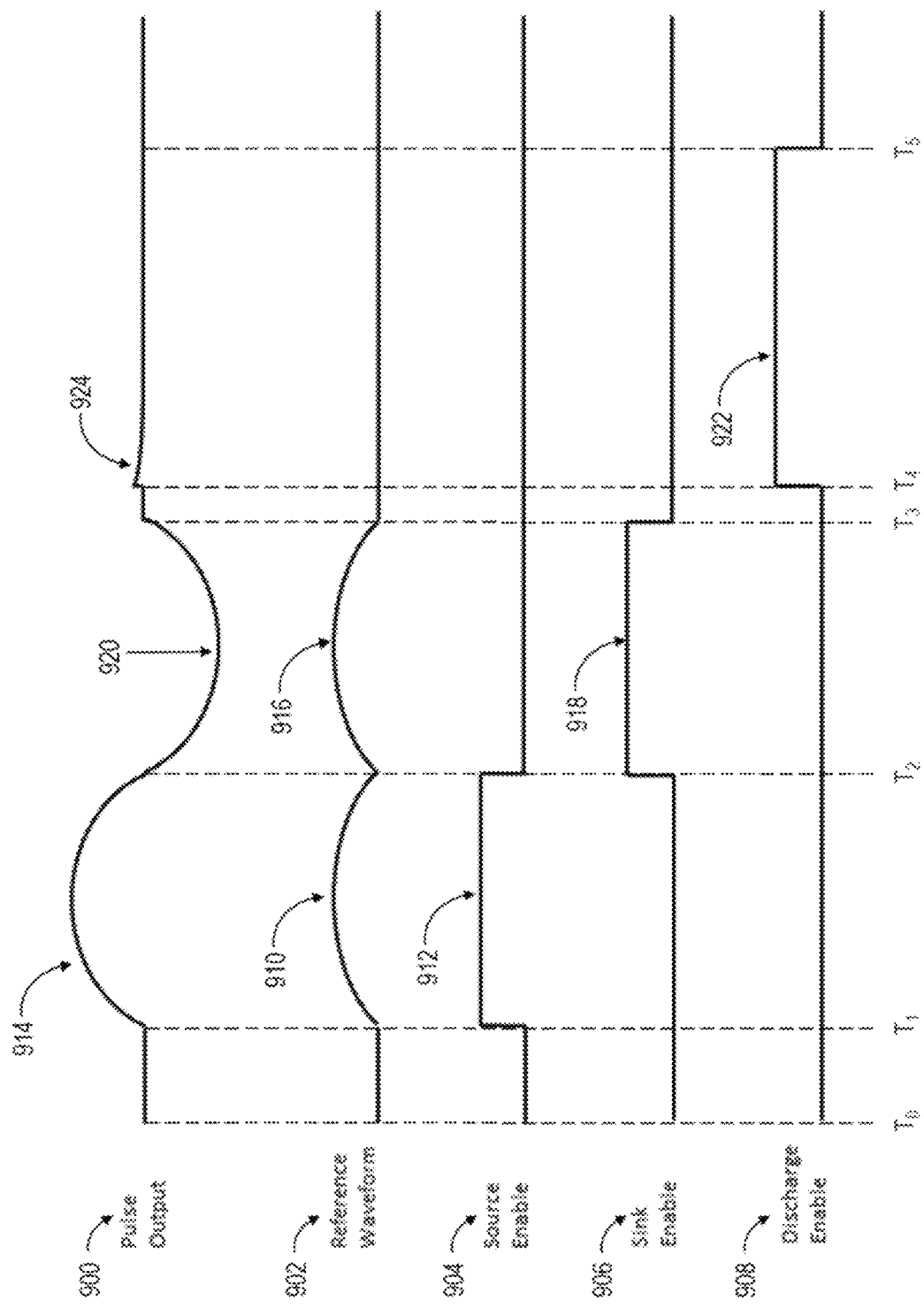
FIG. 9 is an example of an electrical stimulation pulse output and the underlying signals used to form the pulse output in accordance with another embodiment of the subject application.

With reference to FIG. 8 and FIG. 9, example pulse outputs 800, 900 are shown based on the digital signals provided by the controller 102 and the corresponding signals generated by the output pulse circuitry 106. In particular, the pulse output 800, 900 is formed by a reference waveform 802, 902, source-enable signal 804, 904, sink-enable signal 806, 906, and a discharge enable signal 808, 908 are shown. In some embodiments, the reference waveform signal 802, 902 may be a rectangular reference waveform signal 802, or may be a non-rectangular reference waveform signal 902.

With reference to FIG. 8, at a time $T_0$, none of the signals 802, 804, 806, 808 are active. From time $T_1$ to time $T_2$, the reference waveform 802 has a first stimulation phase 810, and the source-side enable signal 804 has an activated phase 812 (i.e. allowing current to source). This corresponds to a stimulation pulse 814 (i.e. to be delivered by one or more channels of the output pulse circuitry 106 via a corresponding one or more electrodes 108). From time $T_2$ to time $T_3$, none of the signals 802, 804, 806, 808 are active, which corresponds to an interphase delay period 816 of the output pulse 800. From time $T_3$ to time $T_4$, the reference waveform 802 has a second stimulation phase 818, and the sink-side enable signal 806 has an activated phase 820 (i.e. allowing current to sink). This corresponds to a charge-balancing phase 822 of the pulse output 800. From time $T_4$ to time $T_5$, none of the signals 802, 804, 806, 808 are active. From time $T_5$ to $T_6$, the discharge enable signal 808 has an active phase 824, thereby allowing any charge built-up in the output channel to dissipate. This corresponds to a passive correction phase 826 of the output pulse 800, used to discharge any charge built-up at the channel output 226, 326, 426, 526, 626, 726.

With reference to FIG. 9, at a time $T_0$, none of the signals 902, 904, 906, 908 are active. From time $T_1$ to time $T_2$, the reference waveform 902 has a first stimulation phase 910, and the source-side enable signal 904 has an active phase 912. The first stimulation phase 910 may be non-rectangular, as shown. This corresponds to a non-rectangular stimulation pulse 914 (i.e. to be delivered by one or more channels of the output circuitry 106 via a corresponding one or more electrodes 108). From time $T_2$ to time $T_3$, the source-side enable signal 904 is not active, however, the reference waveform 902 has a second stimulation phase 916 and the sink-side enable signal 906 has an active phase 918. This corresponds to a non-rectangular charge-balancing phase 920 of the pulse output 900. From time $T_3$ to time $T_4$, none of the signals 902, 904, 906, 908 are active. Then, from time $T_4$ to time $T_5$, the discharge enable signal 908 has an active phase 922, which corresponds to a passive correction phase 924 of the output pulse 900.

Figure 10:
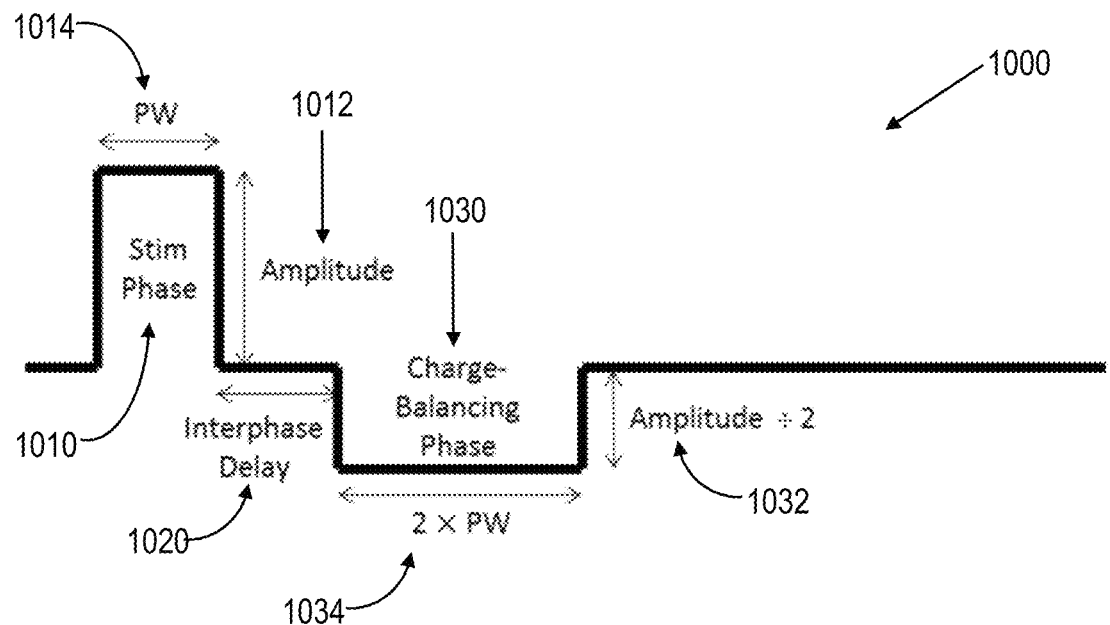
FIG. 10 is a sample of an electrical simulation pulse in accordance with one embodiment of the subject application.

With reference to FIG. 10, an example biphasic output pulse 1000 is illustrated in more detail. In particular, the output pulse 1000 has a first stimulation phase 1010 having an amplitude 1012 and a pulse width 1014. As discussed above, the amplitude of the stimulation phase 1010 may be independently modulated because the source-side amplitude control 222, 322, 422, 522, 622, 722 can be independently programmed. Then, the output pulse 1000 has an interphase delay period 1020, followed by a charge-balancing phase 1030. The charge-balancing phase 1030 can have an amplitude 1032 and a pulse width 1034. The amplitude 1032 of the charge-balancing phase 1030 can also be independently modulated because the sink-side amplitude control 224, 324, 424, 524, 624, 724 can be independently programmed. In particular embodiments, the amplitude 1032 and pulse width 1034 of the charge-balancing phase 1030 may be related to the amplitude 1012 and pulse width 1014 of the stimulation phase 1010. For example, in some embodiments, the amplitude 1032 of the charge-balancing phase 1030 may be half of the amplitude 1012 of the stimulation phase 1010, while the pulse width 1034 of the charge-balancing phase 1030 can be double the pulse width 1014 of the stimulation phase 1010. However, various other combinations of amplitudes 1012, 1032 and pulse widths 1014, 1034 are contemplated.

Figure 11:
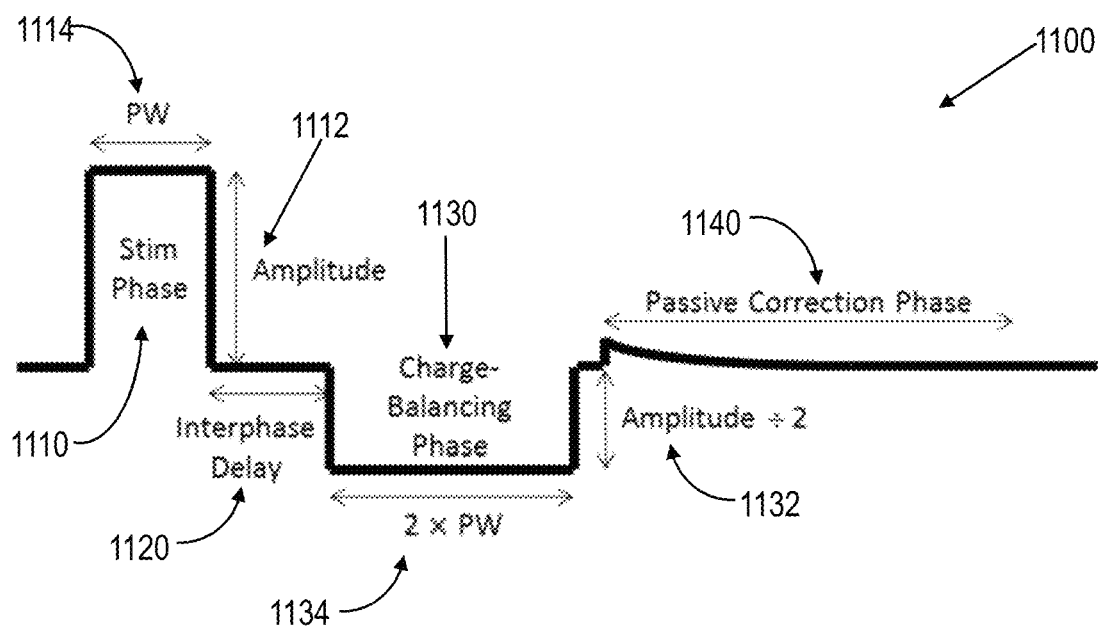
FIG. 11 is a sample of an electrical stimulation pulse in accordance with another embodiment of the subject application.

With reference to FIG. 11, an example three-phase output pulse 1100 is illustrated in more detail. In particular, the output pulse 1100 has a first stimulation phase 1110 having an amplitude 1112 and pulse width 1114. As discussed above, the amplitude of the stimulation phase 1110 may be independently modulated because the source-side amplitude control 222, 322, 422, 522, 622, 722 can be independently programmed. Then, the output pulse 1100 has an interphase delay period 1120, followed by a charge-balancing phase 1130 and a passive correction phase 1140. The charge-balancing phase 1130 can have an amplitude 1132 and a pulse width 1134. The amplitude 1132 of the charge-balancing phase 1130 can also be independently modulated because the sink-side amplitude control 224, 324, 424, 524,

624, 724 can be independently programmed. In particular embodiments, the amplitude 1132 and pulse width 1134 of the charge-balancing phase 1030 may be related to the amplitude 1112 and pulse width 1114 of the stimulation phase 1110. For example, in some embodiments, the amplitude 1132 of the charge-balancing phase 1130 may be half of the amplitude 1112 of the stimulation phase 1110, while the pulse width 1134 of the charge-balancing phase 1130 can be double the pulse width 1114 of the stimulation phase 1110. However, various other combinations of amplitudes 1112, 1132 and pulse widths 1114, 1134 are contemplated.

Returning to FIG. 1, the system 100 may deliver one or more electrical stimulation pulses to, for example, a patient using the system 100, via one or more electrodes 108A, 108B, 108C, 108D connected to one or more output channels 226, 326, 426, 526, 726 of the output circuitry 106. In various embodiments, the electrical stimulation pulses are generated by the output circuitry 106 based on various parameters (e.g. digital source-side enable signal, digital sink-side enable signal, digital discharge enable signal, digital reference waveform, etc.) determined by the controller 102.

In particular embodiments, the same reference waveform may be provided to one or more output channel circuits 200, 300, 400, 500, 600, 700 of an output circuitry 106. However, because each output channel circuit 200, 300, 400, 500, 600, 700 may be independently adjusted, each of the output channel circuits 200, 300, 400, 500, 600, 700 may deliver unique output pulses (e.g. output pulse 800, 900, 1000, 1100) based on the same reference waveform.

For example, in accordance with one embodiment of the present disclosure, in a system 100 having output pulse circuitry 106 comprising at least a first output channel circuit 200, 300, 400, 500, 600, 700 and a second output channel circuit 200, 300, 400, 500, 600, 700, the first output channel circuit 200, 300, 400, 500, 600, 700 may deliver a first output pulse (e.g. pulse 800, 900, 1000, 1100) based on a reference waveform, while the second output channel circuit 200, 300, 400, 500, 600, 700 may deliver a second (i.e. different) output pulse (e.g. pulse 800, 900, 1000, 1100) based on the same reference waveform. For example, the first and second output pulses may have different stimulation phases (i.e. stimulation 1010, 1110) with different amplitudes (i.e. amplitudes 1012, 1112) or different pulse widths (i.e. pulse widths 1014, 1114). The first and second output pulses may have different interphase delay periods (i.e. interphase delay periods 1020, 1120), or different charge-balancing phases (i.e. charge-balancing phases 1030) with different amplitudes (i.e. amplitudes 1032, 1132) or pulse widths (i.e. pulse widths 1034, 1134). Further, the first and second output pulses may have different passive-correction phases (i.e. passive correction phase 1140), or one (or more) of the output pulses may not have a passive-correction phase (e.g. output pulse 1000).

Stimulation Safety Monitor

Turning now to FIG. 12, the safety monitoring circuit 117, 1217 is described in more detail. As illustrated, a second embodiment of the neurostimulation system 1200 is provided. The system 1200 includes a controller 1202 operatively connected to stimulation control logic 1206, a plurality of output channels 1222A, 1222B, 1222C, 1222D operatively connected to the stimulation control logic 1206, and a safety monitor 1217 operatively connected to the controller 1202 and the stimulation control logic 1206.

In particular embodiments, the controller 100, 1202 includes a timing source 1270 for controlling stimulation pulse width (e.g. pulse widths 1014, 1034, 1114, 1134) and pulse rate, digital registers 1272 (e.g. memory 112) that contain pulse parameter information, stimulation instructions 1274 that can be stored in the memory of the controller (e.g. memory 112), and a state machine 1276 for controlling the stimulation output channels 200, 300, 400, 500, 600, 700.

The safety monitor 1217 may receive as inputs 115, 1225 the signals output from the controller 1202 used by the stimulation control logic 1206 to control the electrical stimulation pulses delivered by the output channels 1222A, 1222B, 1222C, 1222D. Collectively, these signals generated by and received from the controller 1202 may be a stimulation pulse signal. More particularly, these signals include one or more of: a digital reference waveform; a digital source-side enable signal; a digital sink-side enable signal; and a digital discharge enable signal. As seen in FIG. 8 and FIG. 9, the combination of these signals can be used to create various stimulation phases in the electrical stimulation pulses delivered by the output channels 1222A, 1222B, 1222C, 1222D. For example, there may be a first phase 1280, a second phase 1282, and an optional third phase 1284. In particular embodiments, the first phase 1280, second phase 1282, and third 1284 are formed based on a combination of one or more of the following signals: a digital reference waveform (e.g. signal 802, 902); a digital source-enable signal (e.g. signals 804, 904); a digital sink-side enable signal (e.g. signals 806, 906); and a digital discharge enable signal (e.g. signals 808, 908).

In some embodiments, the first phase 1280 corresponds to a stimulation phase (e.g. stimulation phases 814, 914, 1010, 1110) of an electrical output pulse (e.g. pulses 800, 900, 1000, 1110), the second phase 1282 corresponds to a charge-balancing phase (e.g. charge-balancing phases 822, 922, 1030, 1130) of an electrical output pulse (e.g. pulses 800, 900, 1000, 1110), and the optional third phase 1284 corresponds to a passive correction phase (e.g. 826, 926, 1132) of an electrical output pulse (e.g. pulses 800, 900, 1110).

Based on the inputs 1225 received (e.g. parameters relating forming phases 1280, 1282, 1284), the safety monitor 117, 1217 can be configured to detect harmful fault conditions and to output a stimulation disable signal 1219 to the output pulse circuitry 106, 1206 that prevents one or more output channel circuits 200, 300, 400, 500, 600, 700 from delivering an electrical pulse that would be harmful due to the fault condition. In particular, the safety monitor 117, 1217 is capable of detecting harmful timing faults that can occur due to hardware or software errors related to the timing source 1270, or when stimulation pulse phases are skipped or performed out-of-order due to a hardware or software fault, or when pulse phases are overlapping due to a hardware or software fault. Further, the safety monitor 117, 1217 is capable of detecting cumulative errors that cannot be detected by other safety architectures.

With reference to FIG. 1, FIG. 12, and FIGS. 13A-13H, the safety monitoring circuit 117, 1217 may include a plurality of error detection circuits 1302, 1304, 1306, 1308, 1310, 1312, 1314, and a stimulation disable logic circuit 1316 operatively connected to one or more of the plurality of error detection circuits 1302, 1304, 1306, 1308, 1310, 1312, 1314.

Figure 13A:
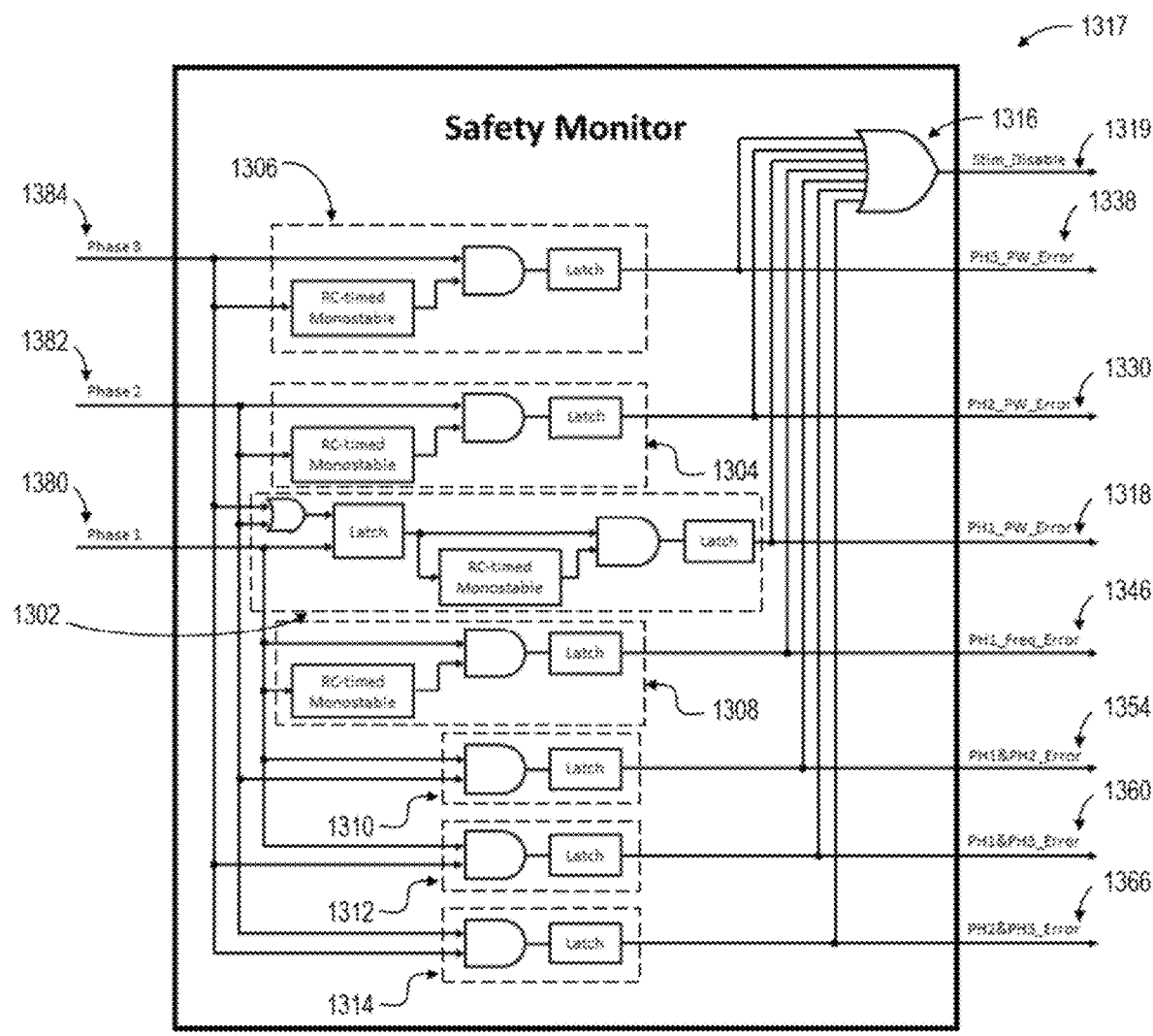
FIGS. 13A-13H are block diagrams of a safety monitor in accordance with one embodiment of the subject application.

With reference to FIG. 13A, in particular embodiments, the plurality of error detection circuits 1302, 1304, 1306, 1308, 1310, 1312, 1314 includes one or more of the following: a first phase error detection circuit 1302; a second phase error detection circuit 1304; a third phase error detection circuit 1306; a stimulation pulse rate error detection circuit 1308; a first overlap error detection circuit 1310;

a second overlap error detection circuit 1312; and a third overlap error detection circuit 1314.

Figure 13B:
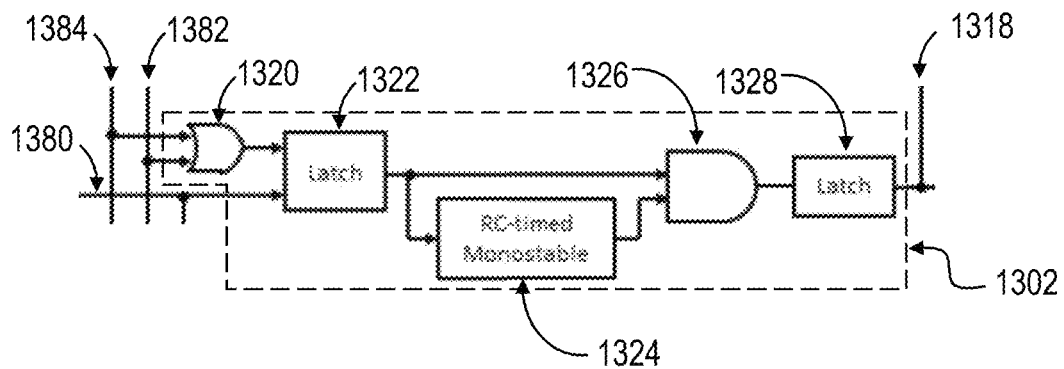

With reference to FIG. 13A and FIG. 13B, the first phase error detection circuit 1302 may be configured to detect whether a pulse width of the first phase 1380 has exceeded a first maximum limit. The first phase error detection circuit 1302 may further be configured to detect whether the second phase 1382 fails to start. The first phase error detection circuit 1302 may receive as inputs the first phase 1380, second phase 1382, and if present, the third phase 1384. The first phase error detection circuit 1302 may output a first phase error signal 1318 to the stimulation disable logic circuit 1316. If a phase error is detected, then the first phase error signal 1318 signals to the stimulation disable logic circuit 1316 that the electrical stimulation output pulse should be prevented, for example, by suppressing the output of all channels.

In particular embodiments, the first phase error detection circuit 1302 can comprise: a first logic circuit 1320; a first latch 1322; an RC-timed monostable 1324; a second logic circuit 1326; and a second latch 1328. The first logic circuit 1320 may be operatively connected to the first latch 1322, and may receive as inputs the second phase 1382 and third phase 1384. The first latch 1322 may be operatively connected to the RC-timed monostable 1324 and the second logic circuit 1326, and may receive as inputs the output from the first logic circuit 1320 and the first phase 1380. The RC-timed monostable 1324 may be operatively connected to the second logic circuit 1326, and may receive as an input the output from the first latch 1322. The second logic circuit 1326 may be operatively connected to the second latch 1328, and may receive as inputs the output from the first latch 1322 and the output from the RC-timed monostable 1324. Finally, the second latch 1328 may be operatively connected to the stimulation disable logic circuit 1316 of the safety monitor 1317. The second latch 1328 may receive as an input the output from the second logic circuit 1326, and may output a first phase error signal 1318.

Figure 13C:
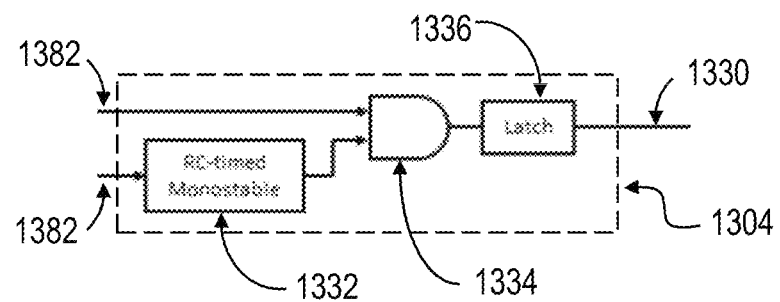

With reference to FIG. 13A and FIG. 13C, the second phase error detection circuit 1304 may be configured to detect whether a pulse width of the second phase 1382 has exceeded a second maximum limit. The second phase error detection circuit 1304 may receive as an input the second phase 1382, and can output a second phase error signal 1330. If a phase error is detected, then the second phase error signal 1330 signals to the stimulation disable logic circuit 1316 that the electrical stimulation output pulse should be prevented, for example, by suppressing the output of all channels.

In particular embodiments, the second phase error detection circuit 1304 can comprise: an RC-timed monostable 1332; a first logic circuit 1334; and a first latch 1326. The RC-timed monostable 1332 may be operatively connected to the first logic circuit 1334, and may receive as an input the second phase 1382. The first logic circuit 1334 may be operatively connected to the first latch 1336, and may receive as inputs the output of the RC-timed monostable 1332 and the second phase 1382. The first latch 1336 may be operatively connected to the stimulation disable logic circuit 1316 off the safety monitor 1317. The first latch 1336 may receive as an input the output of the first logic circuit 1334, and may output the second phase error signal 1330.

Figure 13D:
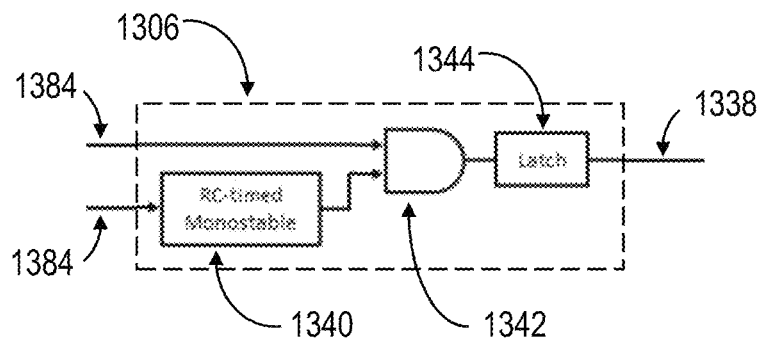

With reference to FIG. 13A and FIG. 13D, the third phase error detection circuit 1306 may be configured to detect whether a pulse width of the third phase 1384 has exceeded a third maximum limit. The third phase error detection circuit 1306 may receive as an input the third phase 1384, and can output a third phase error signal 1338. If a phase error is detected, then the first phase error signal 1338 signals to the stimulation disable logic circuit 1316 that the electrical stimulation output pulse should be prevented, for example, by suppressing the output of all channels.

In particular embodiments, the third phase error detection circuit 1306 can comprise: an RC-timed monostable 1340; a first logic circuit 1342; and a first latch 1344. The RC-timed monostable 1340 may be operatively connected to the first logic circuit 1342, and may receive as an input the third phase 1384. The first logic circuit 1342 may be operatively connected to the first latch 1344, and may receive as inputs the output of the RC-timed monostable 1340 and the third phase 1384. The first latch 1344 may be operatively connected to the stimulation disable logic circuit 1316 off the safety monitor 1317. The first latch 1344 may receive as an input the output of the first logic circuit 1342, and may output the third phase error signal 1338.

Figure 13E:
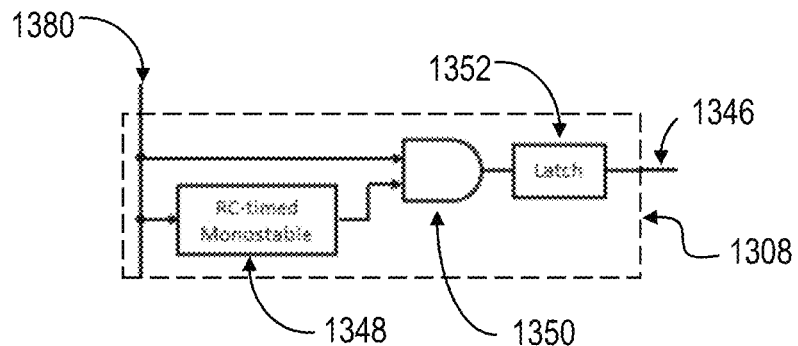

With reference to FIG. 13A and FIG. 13E, the stimulation pulse rate error detection circuit 1308 may be configured to detect whether a pulse rate of the first phase 1380 has exceeded a fourth maximum limit. The stimulation pulse rate error detection circuit 1308 may receive as an input the first phase 1380, and output a stimulation pulse rate error signal 1346. If a stimulation pulse rate error is detected, then the stimulation pulse rate error signal 1346 signals to the stimulation disable logic circuit 1316 that the electrical stimulation output pulse should be prevented, for example, by suppressing the output of all channels.

In particular embodiments, the stimulation pulse rate error detection circuit 1308 can comprise: an RC-timed monostable 1348; a first logic circuit 1350; and a first latch 1352. The RC-timed monostable 1348 may be operatively connected to the first logic circuit 1350, and may receive as an input the first phase 1380. The first logic circuit 1350 may be operatively connected to the first latch 1352, and may receive as inputs the output of the RC-timed monostable 1348 and the first phase 1382. The first latch 1352 may be operatively connected to the stimulation disable logic circuit 1316 off the safety monitor 1317. The first latch 1352 may receive as an input the output of the first logic circuit 1350, and may output the stimulation pulse rate error signal 1346.

With respect to the first, second, third, and fourth maximum limits, these values can be independently set and adjusted, and may be dependent on, for example and without limitation, the maximum stimulation amplitude (current and voltage) achievable by the system and/or the size of the electrodes used to deliver output pulses. In particular embodiments, the pulse rate maximum limits may be from about 50 to about 150 pulses per second, for example. However, other ranges and rates are contemplated. Additionally, the pulse width (i.e. time) for each phase may be limited. For example, in some embodiments, the first phase may be limited to from about 500 to about 600 µs and the pulse width (i.e. time) for the second phase may be limited to from about 900 µs to about 1100 µs; however, other ranges and durations are contemplated.

Figure 13F:
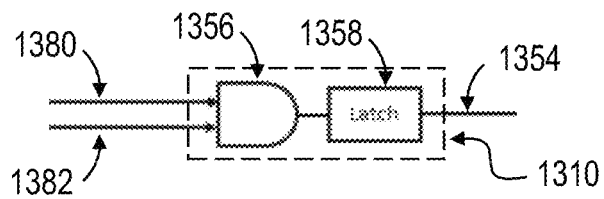

With reference to FIG. 13A and FIG. 13F, the first overlap error detection circuit 1310 may be configured to detect whether the first phase 1380 and second phase 1382 have been incorrectly activated at the same time. The first overlap error detection circuit 1310 may receive as inputs the first phase 1380 and the second phase 1382, and can output a first overlap error signal 1354. If an overlap error is detected, then the first overlap error signal 1354 signals to the stimu- lation disable logic circuit 1316 that the electrical stimulation output pulse should be prevented, for example, by suppressing the output of all channels.

In particular embodiments, the first overlap error detection circuit 1310 can comprise a first logic circuit 1356 operatively connected to a first latch 1358. The first logic circuit 1356 may receive the first phase 1380 and the second phase 1382 as inputs. The first latch 1358 may receive the output from the first logic circuit 1356 as an input, and output the first overlap error signal 1354 to the stimulation disable logic circuit 1316 of the safety monitor 1317.

Figure 13G:
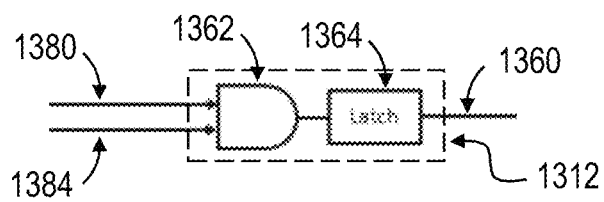

With reference to FIG. 13A and FIG. 13G, the second overlap error detection circuit 1312 may be configured to detect whether the first phase 1380 and third phase 1384 have been incorrectly activated at the same time. The second overlap error detection circuit 1312 may receive as inputs the first phase 1380 and the third phase 1384, and can output a second overlap error signal 1360. If an overlap error is detected, then the second overlap error signal 1360 signals to the stimulation disable logic circuit 1316 that the electrical stimulation output pulse should be prevented, for example, by suppressing the output of all channels.

In particular embodiments, the second overlap error detection circuit 1312 can comprise a first logic circuit 1362 operatively connected to a first latch 1364. The first logic circuit 1362 may receive the first phase 1380 and the third phase 1384 as inputs. The first latch 1364 may receive the output from the first logic circuit 1362 as an input, and output the second overlap error signal 1360 to the stimulation disable logic circuit 1316 of the safety monitor 1317.

Figure 13H:
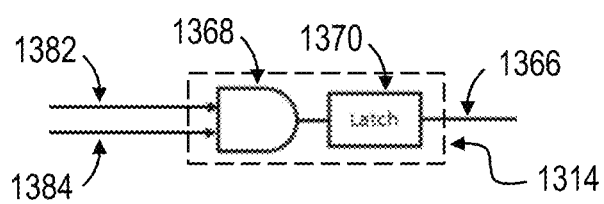

With reference to FIG. 13A and FIG. 13H, the third overlap error detection circuit 1314 may be configured to detect whether the second phase 1382 and the third phase 1384 have been incorrectly activated at the same time. The third overlap error detection circuit 1314 may receive as inputs the second phase 1382 and the third phase 1384, and can output a third overlap error signal 1366. If an overlap error is detected, then the third overlap error signal 1366 signals to the stimulation disable logic circuit 1316 that the electrical stimulation output pulse should be prevented, for example, by suppressing the output of all channels.

In particular embodiments, the third overlap error detection circuit 1314 can comprise a first logic circuit 1368 operatively connected to a first latch 1370. The first logic circuit 1368 may receive the second phase 1380 and the third phase 1384 as inputs. The first latch 1370 may receive the output from the first logic circuit 1368 as an input, and output the third overlap error signal 1366 to the stimulation disable logic circuit 1316 of the safety monitor 1317.

With reference to FIGS. 13A-13H, the logic circuits 1316, 1320, 1326, 1334, 1342, 1350, 1356, 1362, 1368 may comprise one or more logic circuits. In particular embodiments, the logic circuits 1316, 1320, 1326, 1334, 1342, 1350, 1356, 1362, 1368 may include one or more of the following: an AND logic gate; an OR logic gate; a NOT logic gate; a NAND logic gate; a NOR logic gate; an EX-OR logic gate; and an EX-NOR logic gate. For example, in specific embodiments, logic circuit 1320 may be an OR logic gate, and logic circuits 1326, 1334, 1342, 1350, 1356, 1362, 1368 are AND logic gates. In further embodiments, the stimulation disable logic circuit 1316 may be an OR logic gate. In specific embodiments, the stimulation disable logic circuit 1316 may comprise two OR logic gates operatively connected to an OR logic gate, or its equivalent.

In some embodiments, the latches 1322, 1328, 1336, 1344, 1352, 1358, 1364, 1370 may comprise, for example, an S-R latch or a gated S-R latch. For example, in specific embodiments, latches 1322, 1336 may be gated S-R latches, and latches 1328, 1334, 1352, 1358, 1364, 1370 may be S-R latches.

In still further embodiments, the error detection circuits 1302, 1304, 1306, 1308, 1310, 1312, 1314 may include additional components as needed. For example, one or more of the error detection circuits 1302, 1304, 1306, 1308, 1310, 1312, 1314 may include a delay circuit. A delay circuit can delay the input signal received by the delay circuit for a pre-determined period of time, such as from about 50 nanoseconds to about 500 nanoseconds. In some embodiments, the delay period of the delay circuit may be 220 nanoseconds. In specific embodiments, error detection circuits 1302, 1304, 1306, 1308 can include a delay circuit.

Regarding the delay circuit of the error detection circuit 1302, the delay circuit may be operatively connected to the latch 1322 and the logic circuit 1326. The delay circuit may receive the output of the latch 1322 and the logic circuit 1326 may receive the output of the delay circuit as an input.

Regarding the delay circuit of the error detection circuit 1304, the delay circuit may be operatively connected to the logic circuit 1334. The delay circuit may receive the second phase signal 1382 as an input, and the logic circuit 1334 may receive as an input the output of the delay circuit.

Regarding the delay circuit of the error detection circuit 1306, the delay circuit may be operatively connected to the logic circuit 1342. The delay circuit may receive the third phase signal 1384 as an input, and the logic circuit 1342 may receive as an input the output of the delay circuit.

Regarding the delay circuit of the error detection circuit 1308, the delay circuit may be operatively connected to the logic circuit 1352. The delay circuit may receive the first phase signal 1380 as an input, and the logic circuit 1352 may receive as an input the output of the delay circuit.

If one or more error detection signals 1318, 1330, 1338, 1346, 1354, 1360, 1366 are received by the stimulation disable logic circuit 1316 indicating that a harmful error has been detected with respect to one or more phases of an electrical stimulation pulse, then the stimulation disable logic circuit 1316 outputs a stimulation disable signal 1219, 1319 to the stimulation control logic 1206. In other words, at least one of the outputs of the safety monitoring circuit 1217, 1317 is the stimulation disable signal 1219, 1319. In further embodiments, the safety monitor 1217, 1317 may also output the type of error detected 123, 1223 back to the controller 102, 1202. For example, the errors detected 123, 1223 may include the first phase error signal 1318, the second phase error signal 1330, the third phase error signal 1338, the pulse rate error signal 1346, the first overlap signal 1354, the second overlap signal 1360, the third overlap 1366, or any combination thereof. In particular embodiments, the stimulation instructions 1274 may modify future electrical stimulation pulse and/or patterns based on the errors detected 123, 1223.

In further embodiments, one or more aspects of the safety monitor 117, 1217, 1317 may comprise a microcontroller configured to monitor the stimulation control logic 1206 using three inputs (e.g. phases 1280/1380, 1282/1382, 1284/1384). The microcontroller may comprise a processor and memory storing instructions to be executed by the processor. In particular, the instructions may include one or more error detection components, including: a stimulation disable component; a first phase error detection component; a second phase error detection component; a third phase error detection component; a stimulation pulse rate error detection component; a first overlap error detection component; a second overlap error detection component; and a third overlap error detection component.

The first phase error detection component may be configured to detect whether a pulse width of the first phase 1380 has exceeded a first a maximum limit. The first phase error detection component may further be configured to detect whether the second phase 1382 fails to start. The first phase error detection component may receive as inputs the first phase 1380, second phase 1382, and if present, the third phase 1384. The first phase error detection component may output a first phase error signal 1318 to the stimulation disable component. If a phase error is detected, then the first phase error signal 1318 signals to the stimulation disable component that the electrical stimulation output pulse should be prevented.

The second phase error detection component may be configured to detect whether a pulse width of the second phase 1382 has exceeded a second maximum limit. The second phase error detection component may receive as an input the second phase 1382, and can output a second phase error signal 1330. If a phase error is detected, then the second phase error signal 1330 signals to the stimulation disable component that the electrical stimulation output pulse should be prevented, for example, by suppressing the output of all channels.

The third phase error detection component may be configured to detect whether a pulse width of the third phase 1384 has exceeded a third maximum limit. The third phase error detection component may receive as an input the third phase 1384, and can output a third phase error signal 1338. If a phase error is detected, then the first phase error signal 1338 signals to the stimulation disable component that the electrical stimulation output pulse should be prevented, for example, by suppressing the output of all channels.

The stimulation pulse rate error detection component may be configured to detect whether a pulse rate of the first phase 1380 has exceeded a fourth maximum limit. The stimulation pulse rate error detection component may receive as an input the first phase 1380, and output a stimulation pulse rate error signal 1346. If a stimulation pulse rate error is detected, then the stimulation pulse rate error signal 1346 signals to the stimulation disable component that the electrical stimulation output pulse should be prevented, for example, by suppressing the output of all channels.

The first overlap error detection component may be configured to detect whether the first phase 1380 and second phase 1382 have been incorrectly activated at the same time. The first overlap error detection component may receive as inputs the first phase 1380 and the second phase 1382, and can output a first overlap error signal 1354. If an overlap error is detected, then the first overlap error signal 1354 signals to the stimulation disable component that the electrical stimulation output pulse should be prevented, for example, by suppressing the output of all channels.

The second overlap error detection component may be configured to detect whether the first phase 1380 and third phase 1384 have been incorrectly activated at the same time. The second overlap error detection component may receive as inputs the first phase 1380 and the third phase 1384, and can output a second overlap error signal 1360. If an overlap error is detected, then the second overlap error signal 1360 signals to the stimulation disable component that the electrical stimulation output pulse should be prevented, for example, by suppressing the output of all channels.

Finally, the third overlap error detection component may be configured to detect whether the second phase 1382 and the third phase 1384 have been incorrectly activated at the same time. The third overlap error detection component may receive as inputs the second phase 1382 and the third phase 1384, and can output a third overlap error signal 1366. If an overlap error is detected, then the third overlap error signal 1366 signals to the stimulation disable component that the electrical stimulation output pulse should be prevented, for example, by suppressing the output of all channels.

If one or more error detection signals 1318, 1330, 1338, 1346, 1354, 1360, 1366 are received by the stimulation disable component indicating that a harmful error has been detected with respect to one or more phases of an electrical stimulation pulse, then the stimulation disable component outputs a stimulation disable signal 1219, 1319 to the stimulation control logic 1206. In other words, at least one of the outputs of the safety monitor 1217, 1317 is the stimulation disable signal 1219, 1319.

In further embodiments, the safety monitor 1217, 1317 may also output the type of error detected 123, 1223 back to the controller 102, 1202. For example, the errors detected 123, 1223 may include the first phase error signal 1318, the second phase error signal 1330, the third phase error signal 1338, the pulse rate error signal 1346, the first overlap signal 1354, the second overlap signal 1360, the third overlap signal 1366, or any combination thereof. In particular embodiments, the stimulation instructions 1274 may modify future electrical stimulation pulse and/or patterns based on the errors detected 123, 1223.

Figure 14:
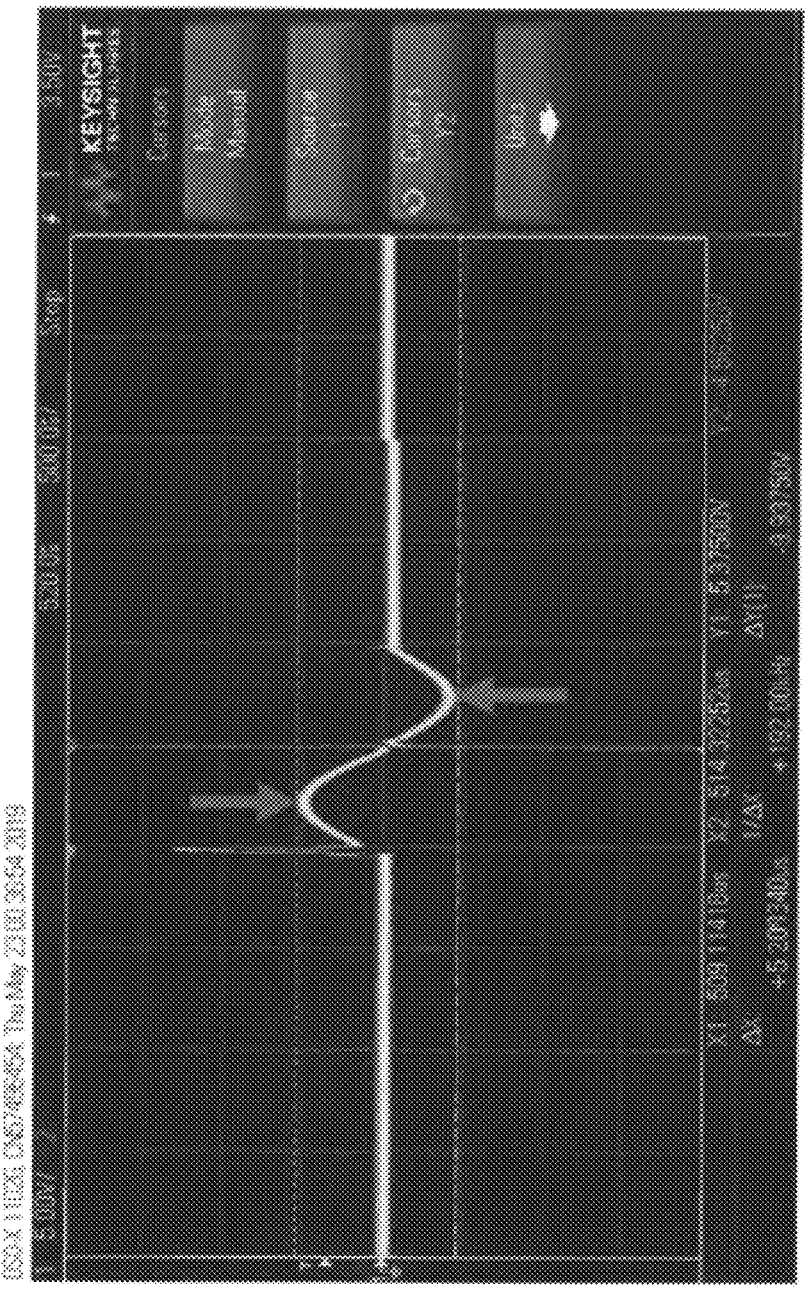
FIG. 14 is a screen-capture of an oscilloscope reading from a electrical stimulation system in accordance with one aspect of the subject application.

In addition to the safety monitor, the stimulation architecture itself provides certain inherent safety benefits by, for example, limiting the output current for one or more of the channels. More specifically, the stimulation control logic 1206 requires that the sources be set to equal and opposite current as the sinks (i.e., cumulative), However, if that condition is not met (i.e., under a single fault condition), then the output current (i.e., stimulation current) may be limited by the minimum current set between the channel pairs. For example, with reference to FIG. 14, a first phase having a sine wave shape and a width of 500 μs and a second phase having a sine wave shape and a 500 μs width were generated and provided to a source channel and a sink channel across an about 9.5 kOhm load. The source channel had a current with an amplitude setting of 20 mA whereas the sink channel had a current with an amplitude setting of 0.5 mA. Because the current to the sources and sinks are not equal and opposite, this stimulates under a single fault condition. As shown in FIG. 14, the first phase signal generates a positive electrical stimulation pulse with an amplitude of 5.375 V, corresponding to 0.57 mA, while the second phase signal generates a negative electrical stimulation pulse with an amplitude of −4.5625 V, corresponding to 0.48 mA, indicating that under this single fault condition, the stimulation current was limited by the minimum current set between the source and sink.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A multi-channel neurostimulation system, comprising:
a high-voltage power supply;
an output pulse circuitry operatively connected to the high-voltage power supply;
a plurality of electrodes operatively connected to the output pulse circuitry; and
a controller operatively connected to the output pulse circuitry, wherein the controller is configured to instruct the output pulse circuitry to deliver an electrical output pulse via one or more of the plurality of electrodes;
wherein the output pulse circuitry comprises a plurality of output channel circuits, each output channel circuit including:
a high-voltage domain having a current source comprising a transistor, a channel output, a DC blocking capacitor operatively connected to the channel output, a discharge switch operatively connected between the DC blocking capacitor and the current source, a discharge enable operatively connected to the discharge switch, and a current mirror; and
a low-voltage domain having a reference current generator, a source-side amplitude control, a current sink comprising a transistor, and a sink-side amplitude control; and
wherein the channel output is operatively connected between the current source and the current sink.

2. The multi-channel neurostimulation system of claim 1, wherein the current source is operatively connected to the high-voltage power supply, the current mirror is operatively connected to the current source and the high-voltage power supply, the reference current generator is operatively connected to the current mirror, the source-side amplitude control is operatively connected to the reference current generator, the current sink is operatively connected to the current source, and the sink-side amplitude control operatively connected to the current sink.

3. The multi-channel neurostimulation system of claim 2, wherein each output channel circuit further includes a first resistor, a second resistor, a source-side cascode element, a source-side enable, a sink-side cascode element, and a sink-side enable;
wherein the high-voltage domain further comprises:
the first resistor operatively disposed between the high-voltage power supply and the current source, wherein the first resistor has a first resistance;
the second resistor operatively disposed between the high-voltage power supply and the current mirror, wherein the second resistor has a second resistance;
the discharge switch operatively disposed between the DC blocking capacitor, the current source, and the sink-side cascode element; and
wherein the second resistance is greater than the first resistance; and
wherein the low-voltage domain further comprises:
the source-side cascode element operatively disposed between the current mirror and the reference current generator;
the source-side enable operatively connected to the source-side cascode element;
the sink-side cascode element operatively disposed between the current source and the current sink; and
the sink-side enable operatively connected to the sink-side cascode element.

4. The multi-channel neurostimulation system of claim 3, wherein each output channel circuit further includes a source-side operational amplifier, a source-side digital potentiometer, a sink-side operational amplifier, and a sink-side digital potentiometer;
wherein the source-side amplitude control comprises:
the source-side operational amplifier operatively connected to the reference current generator; and
the source-side digital potentiometer operatively connected to the source-side operational amplifier; and
wherein the sink-side amplitude control comprises:
the sink-side operational amplifier operatively connected to the current sink; and
the sink-side digital potentiometer operatively connected to the sink-side operational amplifier.

5. The multi-channel neurostimulation system of claim 4, wherein the output pulse circuitry further comprises a reference waveform generator operatively connected to the source-side amplitude control and the sink-side amplitude control of one or more of the plurality of output channel circuits.

6. The multi-channel neurostimulation system of claim 5, wherein one or more of the reference current generator, the current sink, the source-side amplitude control, the current sink, the sink-side amplitude control, the source-side cascode element, the sink-side cascode element, the source-side operational amplifier, the source-side digital potentiometer, the sink-side operational amplifier, and the sink-side digital potentiometer have a voltage rating of about 1.8 V to about 50 V.

7. The multi-channel neurostimulation system of claim 5, wherein one or more of the current source, the current mirror, the first resistor, the second resistor, the DC blocking capacitor, and the discharge switch have a voltage rating of about 20 V to about 1000 V.

8. The multi-channel neurostimulation system of claim 5, wherein the reference waveform generator is operatively connected to the source-side amplitude control and the sink-side amplitude control of each of the plurality of output channel circuits.

9. The multi-channel neurostimulation system of claim 5, wherein the source-side digital potentiometer and the sink-side digital potentiometer of each of the plurality of output channel circuits are individually programmable.

10. The multi-channel neurostimulation system of claim 1, wherein the high-voltage power supply provides a voltage of between about 20 V to about 500 V.

11. The multi-channel neurostimulation system of claim 1, wherein the system further comprises a safety monitor operatively connected to the controller and the output pulse circuitry.

12. The multi-channel neurostimulation system of claim 11, wherein the safety monitor is configured to receive one or more input signals from the controller, and to output a stimulation disable signal to the output pulse circuitry.

13. An electrical stimulation system, comprising:
an output pulse circuitry comprising a plurality of output channel circuits, wherein each output channel circuit is configured to deliver a stimulation pulse;
a controller operatively connected to the output pulse circuitry, wherein the controller is configured to:
generate and deliver a stimulation pulse signal comprising at least a first phase corresponding to a stimulation phase of the stimulation pulse to be delivered by the output pulse circuitry, and a second phase corresponding to a charge-balancing phase of the stimulation pulse to be delivered by the output pulse circuitry; and instruct at least one of the plurality of output channel circuits to deliver the stimulation pulse based on the stimulation pulse signal; and a safety monitor operatively connected to the controller and the output pulse circuitry, wherein the safety monitor is configured to:

receive the stimulation pulse signal generated by the controller; and in response to detection of an error in the received stimulation pulse signal, output a stimulation disable signal to the output pulse circuitry that prevents one or more of the output channel circuits from delivering the stimulation pulse;

wherein the safety monitor is configured to detect the error in the received stimulation pulse signal at least including:

a first phase error in which a pulse width of the first phase of the stimulation pulse signal has exceeded a first maximum limit;

a second phase error in which a pulse width of the second phase of the stimulation pulse signal has exceeded a second maximum limit.

14. The electrical stimulation system of claim 13, wherein the safety monitor is a microcontroller comprising:

a processor; and a memory storing instructions to be executed by the processor;

wherein the instructions includes:

a stimulation disable component configured to output the stimulation disable signal to the output pulse circuitry;

a first phase error detection component configured to detect whether a pulse width of the first phase of the stimulation pulse signal has exceeded a first maximum limit;

a second phase error detection component configured to detect whether a pulse width of the second phase of the stimulation pulse signal has exceeded a second maximum limit;

a third phase error detection component configured to detect whether a pulse width of a third phase of the stimulation pulse signal has exceeded a third maximum limit;

a stimulation pulse rate error detection component configured to detect whether a pulse rate of the stimulation pulse signal has exceeded a fourth maximum limit;

a first overlap error detection component configured to detect whether the first phase and the second phase of the stimulation pulse signal have been incorrectly activated at the same time;

a second overlap error detection component configured to detect whether the first phase and the third phase of the stimulation pulse signal have been incorrectly activated at the same time; and a third overlap error detection component configured to detect whether the second phase and the third phase of the stimulation pulse signal have been incorrectly activated at the same time.

15. The electrical stimulation system of claim 13, wherein the output pulse circuitry receives a stimulation disable signal from the safety monitor and blocks the delivery of a stimulation pulse based on the stimulation disable signal.

16. The electrical stimulation system of claim 13, wherein the safety monitor further comprises:

a plurality of error detection circuits; and a stimulation disable logic circuit operatively connected to the plurality of error detection circuits, the stimulation disable logic circuit being configured to output the stimulation disable signal to the output pulse circuitry;

wherein the plurality of error detection circuits includes:

a first phase error detection circuit configured to detect whether a pulse width of the first phase of the stimulation pulse signal has exceeded a first maximum limit;

a second phase error detection circuit configured to detect whether a pulse width of the second phase of the stimulation pulse signal has exceeded a second maximum limit;

a third phase error detection circuit configured to detect whether a pulse width of a third phase of the stimulation pulse signal has exceeded a third maximum limit;

a stimulation pulse rate error detection circuit configured to detect whether a pulse rate of the stimulation pulse signal has exceeded a fourth maximum limit;

a first overlap error detection circuit configured to detect whether the first phase and the second phase of the stimulation pulse signal have been incorrectly activated at the same time;

a second overlap error detection circuit configured to detect whether the first phase and the third phase of the stimulation pulse signal have been incorrectly activated at the same time; and a third overlap error detection circuit configured to detect whether the second phase and the third phase of the stimulation pulse signal have been incorrectly activated at the same time.

17. The electrical stimulation system of claim 13, wherein the safety monitor receives the stimulation pulse signal from the controller as an input, and wherein the stimulation pulse signal comprises:

a first phase corresponding to a stimulation phase of the stimulation pulse to be delivered; and a second phase corresponding to a charge-balancing phase of the stimulation pulse to be delivered.

18. The electrical stimulation system of claim 17, wherein the stimulation pulse signal further comprises:

a third phase corresponding to a correction phase of the stimulation pulse to be delivered.

19. An output channel circuit for use in an electrical stimulation device, comprising:

a high-voltage domain comprising:

a channel output;

a DC blocking capacitor operatively connected to the channel output;

a current source including a transistor; and a current mirror; and a low-voltage domain comprising:

a reference current generator;

a source-side amplitude control;

a source-side cascode element;

a current sink including a transistor;

a sink-side amplitude control; and a sink-side cascode element;

wherein the channel output is operatively connected between the current source and the current sink.

20. The output channel circuit of claim 19, wherein the high-voltage domain further comprises:

a discharge switch operatively connected between the DC blocking capacitor and the current source; and a discharge enable operatively connected to the discharge switch.

\* \* \* \* \*